(12) United States Patent
Hacker et al.

(10) Patent No.: US 7,216,001 B2
(45) Date of Patent: May 8, 2007

(54) APPARATUS FOR INTRAOPERATIVE NEURAL MONITORING

(75) Inventors: David C. Hacker, Jacksonville, FL (US); Stanley A. Skinner, Wayzata, MN (US); Ensor E. Transfeldt, Edina, MN (US); Peter P. Sterrantino, Jacksonville, FL (US); Lionel Rupp, Bohemia, NY (US)

(73) Assignee: Medtronic Xomed, Inc., Jacksonville, FL (US)

( * ) Notice: Subject to any disclaimer, the term of this patent is extended or adjusted under 35 U.S.C. 154(b) by 382 days.

(21) Appl. No.: 10/754,493

(22) Filed: Jan. 12, 2004
(Under 37 CFR 1.47)

(65) Prior Publication Data
US 2005/0085743 A1   Apr. 21, 2005

Related U.S. Application Data

(60) Provisional application No. 60/441,471, filed on Jan. 22, 2003.

(51) Int. Cl.
*A61N 1/00* (2006.01)
(52) U.S. Cl. .................................................. 607/63
(58) Field of Classification Search ................ 607/43, 607/48, 63, 72, 74; 128/905
See application file for complete search history.

(56) References Cited

U.S. PATENT DOCUMENTS

| | | | |
|---|---|---|---|
| 4,373,531 A | 2/1983 | Wittkampf et al. | |
| 4,892,105 A | 1/1990 | Prass | |
| 4,895,152 A | 1/1990 | Callaghan et al. | |
| 5,161,533 A | 11/1992 | Prass et al. | |
| 6,224,549 B1 * | 5/2001 | Drongelen | ................. 600/300 |
| 6,292,701 B1 | 9/2001 | Prass et al. | |
| 6,306,100 B1 | 10/2001 | Prass | |
| 6,334,068 B1 | 12/2001 | Hacker | |
| 2002/0183647 A1 | 12/2002 | Gozani et al. | |

FOREIGN PATENT DOCUMENTS

WO   WO 02/082982 A1   10/2002

OTHER PUBLICATIONS

Viasys Healthcare, "Multi-Mode Program Plus (MMP Plus) User Guide", Part Number 269-570600, Jun. 2000.*
Burneo, Jorge G, M.D. et al, "Somatosensory Evoked Potentials: Clinical Applications," www.emedicine.com/neuro/topic344.htm.

(Continued)

*Primary Examiner*—Robert Pezzuto
*Assistant Examiner*—Yun Haeng Lee

(57) ABSTRACT

An intraoperative neural monitoring system includes a power source and a simulator powered by the power source to deliver a cycle of electrical stimulation to a patient as a first group of positive or negative phase pulses automatically followed by a second group of pulses of opposite phase or polarity to the pulses of the first group. An activation performed to initiate delivery of the first group of pulses is effective to deliver the entire cycle of stimulation. A method of intraoperative neural monitoring involves activating a simulator to deliver a biphasic cycle of electrical stimulation to a patient during an operative procedure, delivering the entire cycle of electrical stimulation to the patient in response to the activating step and detecting EMG activity in the patient.

27 Claims, 27 Drawing Sheets

OTHER PUBLICATIONS

Stephen, John P., MB, BS, Fracs et al, "Cotrel-Dubousset Instrumentation in Children Using Simultaneous Motor and Somatosensory Evoked Potental Monitoring," SPINE, vol. 21, No. 21, pp. 2450-2457, 1996.

Soliman, Emad, MD, Ph.D. et al, "Somatosensory Evoked Potentials: General Principals, " www.emedicine.come/NEURO//topic640.htm.

Moore, Linda R.T.T., R.EPT, et al, "Intraoperative Monitoring During Surgery for Spinal Deformity," Nicolet Biomedical, Inc. Article No. 169-410300.

Owen, Jeffrey, Ph.D., "Benefits of Multi-Modality ION: Four Case Studies," Nicolet Biomedical, Inc. Article No. 169-410500.

Hartmann, R., et al, "Evoked Potentials from the Auditory Nerve Following Sinusoidal Electrical Stimulatio of the Cochlea: New Possibilities for Preoperative testing in Cochlear-Implant Candidates," Acta Otaolaryngol 1994, 114, pp. 495-500.

Digitimer, Ltd, "Digitimer Multipulse Stimulator D185 Operator's Manual," Issue 6, 2003.

Digitimer, Ltd., "Digitimer Isolated Multipulse Stimulator Model D 185, Operator's Manual", Issue 4, 1999.

Ubags LH, Kalkman CJ, Been HD, Koelman JH, Ongerboer de Visser BW, A comparison of myogenic motor evoked responses to electrical and magnetic transcranial stimulation during nitrous oxide/opioid anesthesia., Anesth Analg 88: 3, 568-72, Mar. 1999.

Gokaslan ZL, Samudrala S, Deletis V, Wildrick DM, Cooper PR, Intraoperative monitoring of spinal cord function using motor evoked potentials via transcutaneous epidural electrode during anterior cervical spinal surgery., J Spinal Disord 10: 4, 299-303, Aug. 1997.

Digitimer, Ltd., D 185 Brochure, May 8, 2001.

Kothbauer K, Deletis V, Epstein FJ, Intraoperative spinal cord monitoring for intramedullary surgery: an essential adjunct, Pediatr Neurosurg 26: 5, 247-54, May, 1997.

Haghighi SS, Gaines RW, Repetitive vs. single transcranial electrical stimulation for intraoperative monitoring of motor conduction in spine surgery., Mo med 100: 3, 262-5, May-Jun. 2003.

Haghighi SS, Monitoring of motor evoked potentials with high intensity repetitive transcranial electrical stimulation during spinal surgery., J Clin Monit Comput 17: 5, 301-8, Jul. 2002.

MacDonald DB, Al Zayed Z, Khoudeir I, Stigsby B, Monitoring scoliosis surgery with combined multiple pulse transcranial electric motor and cortical somatosensory-evoked potentials from the lower and upper extremities., Spine 28: 2, 194-203, Jan. 15, 2003.

Pelosi L, Stevenson M, Hobbs GJ, Jardine A, Webb JK, Intraoperative motor evoked potentials to transcranial electrical stimulation during two anaesthetic regimens., Clin Neurophysiol 112: 6, 1076-87, Jun. 2001.

Kawaguchi M, Inoue S, Kakimoto M, Kitaguchi K, Furuya H, Morimoto T, Sakaki T, The effect of sevoflurane on myogenic motor-evoked potentials induced by single and paired transcranial electrical stimulation of the motor cortex during nitrous oxide/ketamine/fentanyl anesthesia., J Neurosurg Anesthesiol 10: 3, 131-6, Jul. 1998.

Calancie B, Harris W, Broton JG, Alexeeva N, Green BA, "Threshold-level" multipulse transcranial electrical stimulation of motor cortex for intraoperative monitoring of spinal motor tracts: description of method and comparison to somatosensory evoked potential monitoring., J Neurosurg 88: 3, 457-70, Mar. 1998.

Jones SJ, Harrison R, Koh KF , Mendoza N, Crockard HA, Motor evoked potential monitoring during spinal surgery: responses of distal limb muscles to transcranial cortical stimulation with pulse trains., Electroencephalogr Clin Neurophysiol 100: 5, 375-83, Sep. 1996.

Pechstein U, Cedzich C, Nadstawek J, Schramm J, Transcranial high-frequency repetitive electrical stimulation for recording myogenic motor evoked potentials with the patient under general anesthesia., Neurosurgery 39: 2, 335-43; discussion 343-4, Aug, 1996.

Calancie B, Harris W, Brindle F, Green BA and Landy H., "Threshold-level repetitive electrical stimulation for intraoperative monitoring of central motor conduction.", J Neurosurg (Spine 1) 95: 161-168 2001.

Houlden D., "Intraoperative Spinal Cord Monitoring" Part of the Spine Block Curriculum in Neurosurgery—Electrophysiology Section, Feb. 9, 2001.

Digitimer, Ltd., "MultiPulse Stimulator, Model D 185 Service Manual," Issue 4, 1999.

Digitimer, Ltd., D185 Brochure, May 8, 2001.

Jones SJ, Harrison R, Koh KF, Mendoza N. Crockard HA, Motor evoked potential monitoring during spinal surgery: responses of distal limb muscles to transcranial cortical stimulation with pulse trains., Electroencephalogr Clin Neurophysiol 100: 5, 375-83, Sep. 1996.

* cited by examiner

APPARATUS FOR INTRAOPERATIVE NEURAL MONITORING

CROSS-REFERENCE TO RELATED PATENT APPLICATION

This application claims priority from prior provisional patent application Ser. No. 60/441,471 filed Jan. 22, 2003, the entire disclosure of which is incorporated herein by reference.

BACKGROUND OF THE INVENTION

1. Field of the Invention

The present invention relates generally to intraoperative neural monitoring and, more particularly, to apparatus and methods for intraoperative neural monitoring involving monitoring of the spinal cord using motor evoked potentials elicited by electrical stimulation.

2. Brief Discussion of the Related Art

Intraoperative neural monitoring involving intraoperative monitoring of the spinal cord has become accepted as an effective means to avoid neural deficits in patients undergoing various types of surgical procedures in which the spinal cord is at risk of injury. By monitoring the integrity of the spinal cord motor tracts during surgery, impairments in motor function may be detected before they become irreversible and while there is sufficient time to institute corrective measures.

Spinal cord monitoring has traditionally relied on the Stagnara wake-up test, which is ordinarily performed at the conclusion of a surgical procedure and thusly does not provide an early indication of spinal cord dysfunction. Wake-up testing is limited to evaluating gross motor function and fails to identify more subtle spinal cord impairments. Oftentimes administration of the wake-up test is compromised by anesthetic influences. The wake-up test depends on a subjective assessment of a patient's motor responses, and is usually of little value in patients whose motor responses are already impaired by preexisting neural deficits. Additional disadvantages of the wake-up test include the risks of air embolism and self-extubation.

Sensory evoked potentials (SEPs) have also been used for intraoperative spinal cord monitoring, primarily to monitor the dorsal medial tracts within the spinal cord. SEPs are ascending motor volleys elicited by stimulating a peripheral nerve, commonly the posterior tibial nerve at the ankle (medial malleolus), and conducted primarily through the dorsal columns of the spinal cord. SEPs may be detected and recorded as waveforms at various anatomical locations along the nerve tract including peripherally (e.g. popliteal fossa), cervically and cortically. Medically significant changes in amplitude and latency of SEP waveforms during surgery may be indicative of surgically-induced sensory deficits (parathesia). However, it is possible for motor deficits to develop intraoperatively despite the lack of medically significant changes in recorded SEPs, i.e. false negatives. In addition, in some patients it may be difficult or not possible to obtain SEP readings intraoperatively. Being low amplitude, SEP responses require averaging over time such that the readings obtained from SEPs are not as close to real-time as would be desirable. Routine intraoperative spinal cord monitoring using SEPs cannot effectively spatially resolve the loss of certain nerve roots, such as the lumbosacral root, which optimally requires electromyographic (EMG) responses from muscles enervated by the nerve roots.

A more recent form of spinal cord monitoring that addresses many of the disadvantages of the wake-up test and SEPs involves monitoring the spinal cord motor tracts using motor evoked potentials (MEPs). Transcranial electrical stimulation to stimulate the motor cortex has been proposed for eliciting MEPs, which are descending motor volleys conducted along the motor pathways of the spinal cord. The motor cortex can be stimulated non-invasively through an intact skull with electrical current of sufficient magnitude applied via appropriately placed stimulating electrodes. MEPs can be recorded at various anatomical locations including the spine, innervated muscles of the upper and lower extremities (myogenic), and peripheral nerves (neurogenic). Medically significant changes in recorded MEPs during surgery may be indicative of surgically-induced motor deficits (paraplegia), and MEPs are believed to be more sensitive to certain types of spinal cord trauma than SEPs. MEPs recorded from the spinal cord reflect the functional integrity of the corticospinal tract, and MEPs recorded from limb muscles reflect the functional integrity of the motor system from the cerebral cortex to beyond the neuromuscular junction. By stimulating the motor cortex on both sides of the patient's body and recording myogenic MEPs (compound muscle action potential) in muscles on both sides of the patient's body, unilateral neural deficits can be differentiated.

Although magnetic stimulation of the motor cortex can be used to elicit MEPs, transcranial electrical stimulation is generally preferred because magnetic motor evoked potentials are more sensitive to anesthetic-induced depression than electrical motor evoked potentials. Although anesthetics reduce synoptic efficacy and decrease cortical excitability as well as the excitability of spinal motoneurons and interneurons, repetitive or multipulse transcranial stimulation with electrical pulses of sufficiently high current can still elicit MEPs by enhancing temporal summation of the descending input on spinal motoneurons. It is also possible to elicit MEPs by direct electrical stimulation of the spinal cord using epidural electrodes or needle electrodes placed near or in the vertebral bodies with recording accomplished in muscles, nerves and/or the epidural space.

MEPs are large amplitude responses that do not require signal averaging, such that reporting may be accomplished essentially real-time. MEPs provide fast, practical and reliable qualitative information on the functional integrity of the motor tracts of the spinal cord. Because MEPs and SEPs are conducted in different spinal cord pathways having different blood supplies, MEPs may be present in patients when SEPs are absent or ill-defined. MEP monitoring thusly makes it possible to monitor the spinal cord in patients for whom SEP signals are unobtainable. Furthermore, MEPs may better reflect the integrity of the anterior spinal cord than SEPs.

Representative discussions of transcranial electrical stimulation to elicit MEP responses for monitoring the spinal cord during spinal surgery are set forth in "Cotrel-Dubousset Instrumentation in Children Using Simultaneous Motor And Somatosensory Evoked Potential Monitoring" by Stephen, Sullivan, Hicks, Burke, Woodforth and Crawford, "Threshold-level repetitive transcranial electrical stimulation for intraoperative monitoring of central motor conduction" by Calancie, Harris, Brindle, Green and Landy, "A comparison of myogenic motor evoked responses to electrical and magnetic transcranial stimulation during nitrous oxide/opioid anesthesia" by Ubags, Kalkman, Been, Koelman, and de Visser, "Intraoperative monitoring of spinal cord function using motor evoked potentials via transcutaneous epidural electrode during anterior cervical spinal surgery" by Gokaslan, Samudrala, Deletis, Wildrick and Cooper, "Intraoperative spinal cord monitoring for intramedullary surgery: an essential adjunct" by Kothbauer, Deletis and Epstein, "Improved amplitude of myogenic motor evoked responses after paired transcranial electrical stimulation during sufentanil/nitrous oxide anesthesia" by Kalkman, Ubags, Been, Swaan and Drummond, "Repetitive vs. single transcranial electrical stimulation for intraoperative monitoring of motor conduction in spine surgery" by Haghighi and Gaines, "Monitoring of motor evoked potentials with high intensity repetitive transcranial electrical stimulation during spinal surgery" by Haghighi, "Monitoring scoliosis surgery with combined multiple pulse transcranial electric motor and cortical somatosensory-evoked potentials from the lower and upper extremities" by MacDonald, Zayed, Khoudeir and Stigsby, "Intraoperative motor evoked potentials to transcranial electrical stimulation during two anaesthetic regimens" by Pelosi, Stevenson, Hobbs, Jardine and Webb, "The effect of sevoflurane on myogenic motor-evoked potentials induced by single and paired transcranial electrical stimulation of the motor cortex during nitrous oxide/ketamine/fentanyl anesthesia" by Kawaguchi, Inoue, Kakimoto, Kitaguchi, Furuya, Morimoto and Sakaki, "Threshold-level multipulse transcranial electrical stimulation of motor cortex for intraoperative monitoring of spinal motor tracts: description of method and comparison to somatosensory evoked potential monitoring" by Calanci, Harris, Broton, Alexeeva and Green, "Motor evoked potential monitoring during spinal surgery: responses of distal limb muscles to transcranial cortical stimulation with pulse trains" by Jones, Harrison, Koh, Mendoza and Crockard, "Transcranial high-frequency repetitive electrical stimulation for recording myogenic motor evoked potentials with the patient under general anesthesia" by Pechstein, Cedzich, Nadstawek and Schramm, and "Intraoperative Spinal Cord Monitoring" by Houlden. A representative discussion relating to direct electrical stimulation of the spinal cord to elicit MEPs is set forth in "Intra-operative monitoring during surgery for spinal deformity" by Moore and Owen.

Since myogenic MEPs may not indicate motor injury of individual nerve roots, such as the lumbosacral root, it is advantageous in many surgical procedures in which the spinal cord is monitored to also perform neural monitoring involving individual nerve roots. For example, some spinal procedures entail internal fixation with medical devices that may irritate or injure nerve roots, such as the lumbar root, when placed in a patient's body during an operative procedure. Nerve irritation or injury may occur and remain undetected even while standard MEP testing appears normal. It is therefore beneficial to intraoperatively detect dysfunction in individual nerve roots by electrically stimulating the nerve or the anatomical area in the vicinity of the nerve, and monitoring electromyographic (EMG) responses in muscles innervated by the nerve. When electrical stimulation is applied to anatomical tissue at or reasonably near the nerve of interest, the stimulation signal is transmitted through the nerve to excite the related muscle. Excitement of the muscle causes an electrical impulse to be generated within the muscle (EMG) which may be detected by a monitoring or recording electrode in the muscle, thereby providing an indication as to the location and/or integrity of the nerve. Locating a nerve during surgery allows the area of the nerve to be avoided so that it is protected and preserved. Providing an indication of nerve integrity allows nerve irritation or trauma to be detected early, so that the source of irritation or trauma can be identified and corrected. Accordingly, it is beneficial in many types of surgical procedures to perform neural monitoring by monitoring both the spinal cord, using elicited MEPs, and individual nerves/nerve roots, using evoked EMG. The stimulation current for evoked EMG is ordinarily delivered at lower current amperage than the stimulation required to elicit MEPs. In addition to monitoring EMG responses when electrical stimulation is applied, it is also desirable for neural intraoperative monitoring systems to permit neural monitoring involving continuous monitoring of EMG activity from certain muscles at rest and/or when no electrical stimulation is being applied. It would therefore be desirable to provide a single intraoperative neural monitoring system capable of performing multiple modalities of neural monitoring including MEP monitoring and continuous and evoked EMG monitoring.

A representative monitoring or recording electrode for detecting EMG responses in muscles is disclosed in U.S. Pat. No. 5,161,533 to Prass et al. Representative monopolar and bipolar stimulating probes for electrically stimulating a nerve or anatomical tissue in the vicinity of a nerve are disclosed in U.S. Pat. No. 4,892,105 to Prass and U.S. Pat. No. 6,292,701 B1 to Prass et al. Prior nerve integrity monitoring systems for recording EMG activity from muscles and alerting a surgeon when a nerve has been activated by an electric stimulus are represented by U.S. Pat. No. 6,334,068 B1 to Hacker and U.S. Pat. No. 6,306,100 B1 to Prass. The entire disclosures of U.S. Pat. Nos. 4,892,105, 5,161,533, 6,292,701 B1, 6,306,100 B1, and 6,334,068 B1 are incorporated herein by reference.

Prior intraoperative neural monitoring systems are either not designed to provide electrical current of sufficient magnitude to elicit MEPs or are not designed to provide automatic biphasic electrical stimulation sequences between the stimulating electrodes. Biphasic electrical stimulation sequences between stimulating electrodes placed in a patient's body in correspondence with the anatomical areas to be stimulated allow the anatomical areas to be sequentially alternatingly stimulated. Where the stimulated anatomical areas, such as the left and right motor cortex, generate MEPs respectively detectable as EMG responses on opposite sides, i.e. left and right, of the patient's body, unilateral neural deficits can be differentiated. However, where the direction or polarity of current flow between the stimulating electrodes is fixed, providing monophasic electrical stimulation in one direction or polarity between the stimulating electrodes, the anatomical areas cannot be sequentially alternatingly stimulated without manually reversing the locations of the stimulating electrodes with respect to the anatomical areas or electromechanically reversing the lead polarities for the stimulating electrodes each time polarity or direction of current flow between the stimulating electrodes is to be reversed.

The Digitimer D185 Multipulse Stimulator of Digitimer Ltd. allows the direction or polarity of current flow between the stimulating electrodes to be reversed, but not automatically. Rather, a polarity selection switch having "normal" and "reverse polarity" settings must be operated each time the direction or polarity of the stimuli is to be reversed. Operation of the polarity selection switch is in addition to operation of a separate trigger switch that activates the delivery of electrical pulses to the output stimulating electrode. Operation of the trigger switch effects delivery of only one phase (positive or negative) of electrical pulses since the polarity selection switch must be operated in order to deliver pulses of the opposite phase. Another operation of the trigger switch is required to effect delivery of the opposite phase pulses.

Prior intraoperative neural monitoring systems used to elicit MEPs and/or the stimulators used to elicit MEPs are therefore associated with various disadvantages including additional operational steps which increase the duration of the surgical procedures to the detriment of patients and medical personnel, increased complexity and confusion attendant with intraoperative neural monitoring, the possible occurrence of false negative responses due to stimulation on the wrong side of the body, and the need for greater human and/or mechanical intervention. Prior intraoperative neural monitoring systems used to elicit MEPs and/or the stimulators used to elicit MEPs have further drawbacks including failing to provide both positive and negative monophasic and automatic biphasic sequenced outputs from a single stimulator, failing to present left and right EMG waveforms simultaneously and correlated in time to biphasic electrical stimulation to allow a more complete interpretation of neurological motor responses, and the inability to efficiently integrate multiple neural monitoring modalities.

SUMMARY OF THE INVENTION

The present invention is generally characterized in an intraoperative neural monitoring system comprising a power source and a stimulator powered by the power source to deliver a complete cycle of biphasic electrical stimulation to a patient via stimulating electrodes connected to the stimulator and applied to the patient. The complete cycle of biphasic electrical stimulation is delivered from the stimulator as a first group of a selected number of positive phase or negative phase pulses automatically followed by a second group of a selected number of pulses of reverse phase or polarity to the pulses of the first group. The first group of pulses is delivered to a first stimulating electrode for return via a second stimulating electrode in the positive phase and is delivered to the second stimulating electrode for return via the first stimulating electrode in the negative phase. The intraoperative neural monitoring system includes an activator actuatable by a user to perform an activation to initiate delivery of the first group of pulses, and the activation effects delivery of the entire cycle of biphasic electrical stimulation. The stimulator may alternatively be activated to deliver a complete cycle of monophasic electrical stimulation comprising a selected number of pulses that are all positive phase or all negative phase.

Various parameters for the electrical stimulation delivered by the stimulator are selectable including mode, i.e. biphasic or monophasic, current amplitude, pulse width, delay between successive pulses, and number of pulses. The stimulator is capable of delivering electrical stimulation having a current amplitude in the range of 0 to 200 mA to elicit MEPs in the patient. The stimulator is electrically connectible with a power console, which may serve as the power source for the stimulator, and the power console includes a touch screen by which the parameters may be selected. The activator may include a control option on the touch screen or a hand switch.

The intraoperative neural monitoring system may also include a patient interface unit electrically connectible with the power source for delivering electrical stimulation to the patient via a monopolar or bipolar stimulating probe connected to the patient interface unit. The electrical stimulation delivered by the patient interface unit comprises constant current monophasic pulses delivered continuously for so long as a tip of the probe is in contact with anatomical tissue. Various parameters for the electrical stimulation delivered by the patient interface unit, including current amplitude, pulse width, and repetition, are selectable and may be selected via the touch screen. The patient interface unit is capable of delivering electrical stimulation having a current amplitude in the range of 0 to 30 mA to evoke EMG activity in the patient. The patient interface unit comprises a plurality of monitoring channels for the connection of monitoring or recording electrodes to be applied to the patient to detect EMG activity.

The touch screen provides various displays including a setup display, a nerve root selection display, a montage display, monitoring displays and an electrodes display. The monitoring displays display waveforms representative of EMG activity detected by the monitoring electrodes. A monitoring display for electrical stimulation applied via the stimulator includes a waveform display area that displays waveforms representative of EMG activity detected for the positive and negative phases of electrical stimulation, and the waveforms are displayed simultaneously and correlated in time.

The present invention is also generally characterized in a method of intraoperative neural monitoring comprising the steps of activating a stimulator to initiate delivery of a biphasic cycle of electrical stimulation to a patient during an operative procedure, delivering the entire biphasic cycle of electrical stimulation to the patient in response to the activating step, and detecting EMG activity in a muscle of the patient responsive to the electrical stimulation to monitor neural function during the operative procedure. The method may involve eliciting motor evoked potentials in the patient in response to the electrical stimulation. The step of activating may be performed as a two-step procedure executed via a touch screen of a power console connected to the stimulator or via a hand switch connected to the power console. The electrical stimulation may be delivered to the patient at various anatomical locations, and the step of delivering may include delivering the electrical stimulation to the left and right motor cortex and/or to the spinal cord. The step of delivering may include delivering the electrical stimulation to the patient via stimulating electrodes applied to the patient. The method may involve various additional steps including the step of delivering electrical stimulation to the patient via a monopolar or bipolar stimulating probe connected with a patient interface unit that is electrically connected to the power console. The step of detecting may involve detecting the EMG activity via monitoring electrodes placed in muscle of the patient and may involve displaying waveforms representative of the detected EMG activity on a monitoring display of the touch screen Various objects and advantages of the present invention will become apparent from the following description of a preferred embodiment taken in conjunction with the accompanying drawings, wherein like parts in each of the several figures are identified by the same reference characters.

DESCRIPTION OF THE PREFERRED EMBODIMENT

Figure 1:
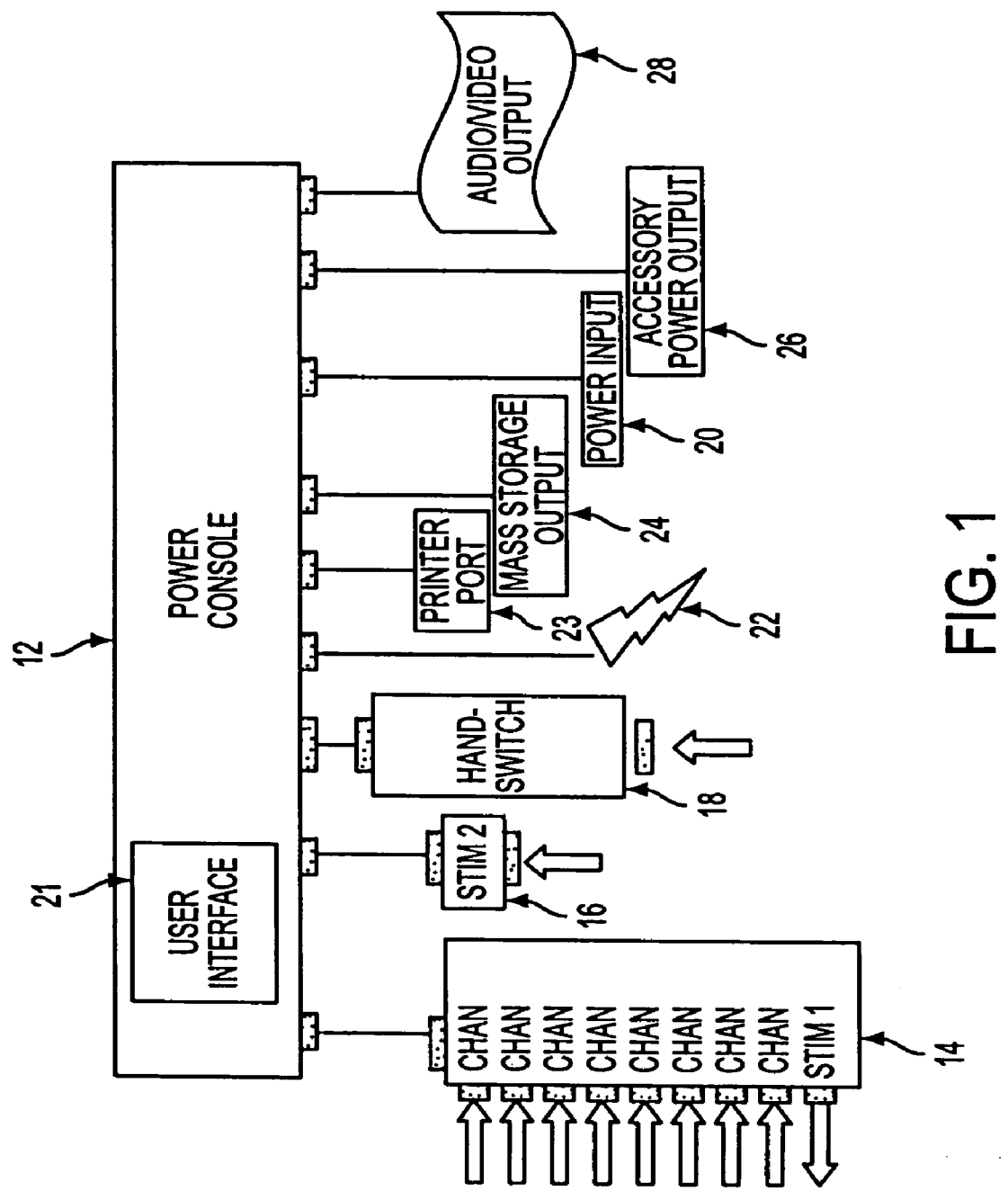
FIG. 1 is a block diagram generally representing an intraoperative neural monitoring system according to the present invention.

An intraoperative neural monitoring system 10 according to the present invention is depicted in FIG. 1 and comprises a power console 12, a patient interface unit 14 for being electrically connected with the power console to deliver Stim 1 electrical stimulation, a stimulator 16 for being electrically connected with the power console to deliver Stim 2 electrical stimulation, a hand switch 18 for controlling activation of Stim 2 electrical stimulation, and a power input 20 for supplying electric power to the power console from a suitable power source. The power console 12 includes a user interface 21 providing multilingual (voice and text) interaction with a user, and preferably the power console includes one or more connectors for connection with one or more muting detectors 22. The power console 12 may include a printer port 23, a mass storage output 24, an accessory power output 26 and/or an audio/video output 28 as explained further below.

Figure 2:
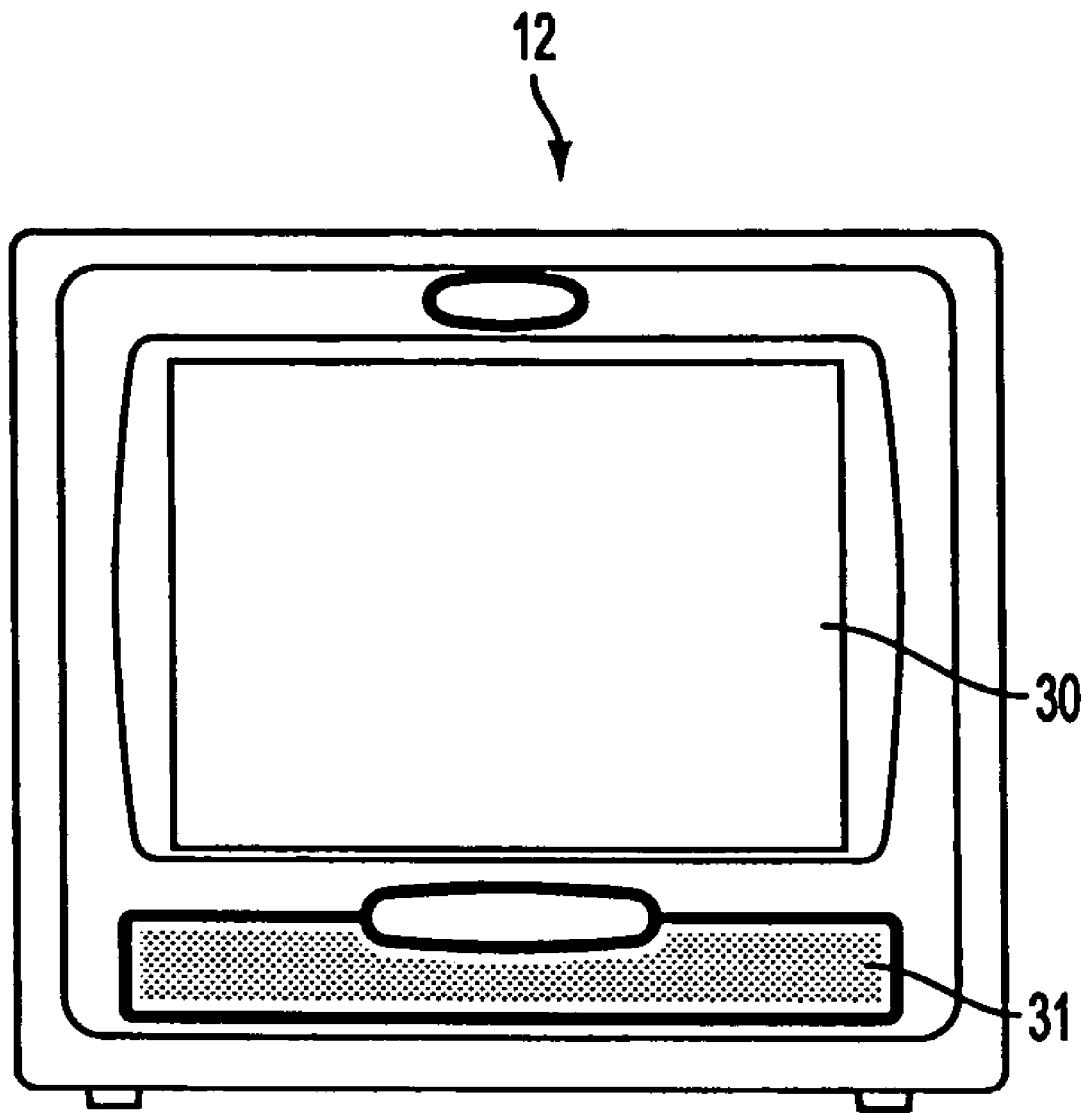
FIG. 2 is a front view of a power console of the intraoperative neural monitoring system.
Figure 3:
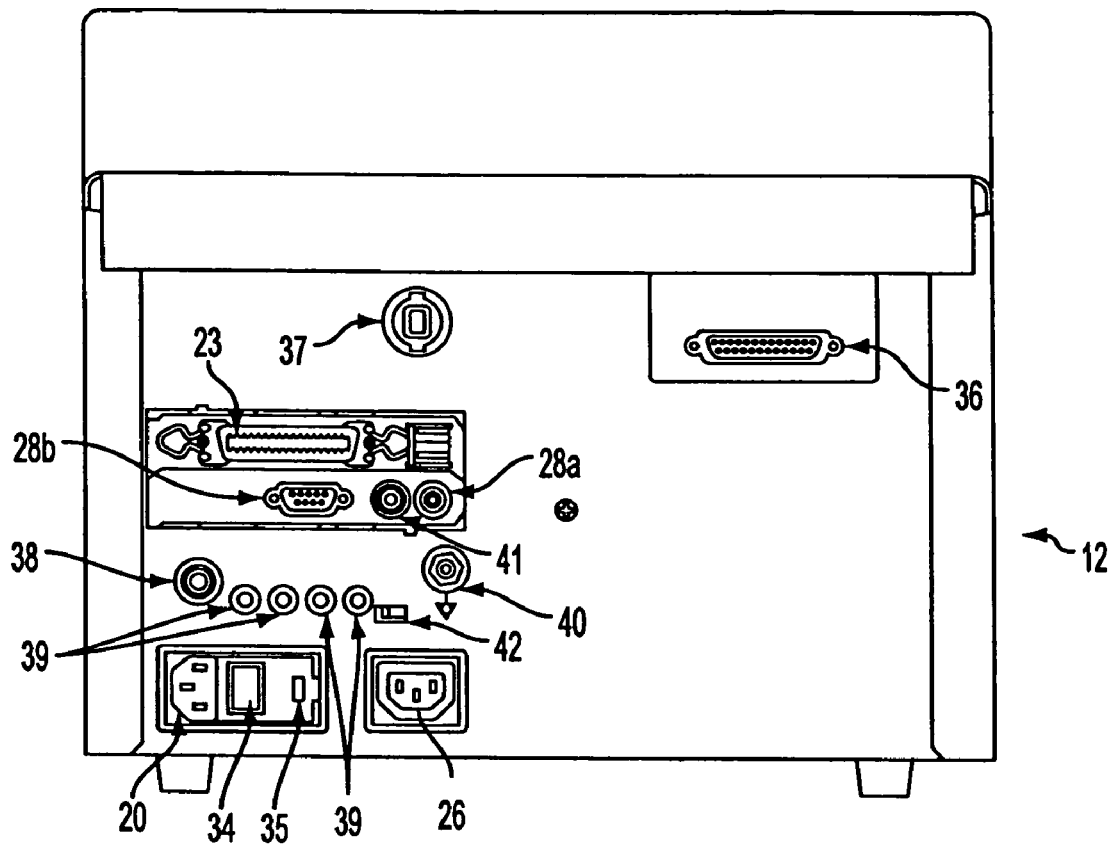
FIG. 3 is a back view of the power console.

The power console 12 is shown in FIGS. 2 and 3. As shown in FIG. 2, the power console 12 comprises a touch screen 30 of the user interface 21 by which various functions of the intraoperative neural monitoring system 10 are controlled and visually displayed, and a speaker 31 of the user interface 21 that provides audible communication with the user. The touch screen 30 will typically be provided on the front of the power console 12, which is depicted in FIG. 2, but could be provided on the power console at any suitable location. As illustrated in FIG. 3, the power input 20 may be an AC power input and may comprise a connector on the power console 12 for receiving the plug of a power cord (not shown) which plugs into a standard AC power outlet, thereby providing electrical power to the power console. A switch 34 may be provided on the power console 12 for selectively turning electrical power to the power console on and off. A fuse access 35 on the power console allows for the removal and replacement of appropriate AC power fuses. Of course, the power console 12 could be provided with a self-contained power source. The power console 12 serves as a power source for the patient interface unit 14 and the simulator 16.

As shown in FIG. 3, the patient interface unit 14 connects to the power console 12 via a patient interface connector 36 on the power console, and the patient interface connector 36 may be a 25 pin D-sub connector. The stimulator 16 connects to the power console 12 via an auxiliary connector 37 on the power console, and the auxiliary connector 37 may be any suitable electrical connector. The hand switch 18 connects to the power console 12 via a hand switch connector 38, such as a head phone jack, on the power console. The one or more muting detectors 22 connect to the power console 12 via one or more muting detector connectors 39 on the power console. Preferably, four muting detector connectors 39 are provided on the power console 12 providing varying levels of gain as explained further below. The power console 12 has a ground element 40.

As further shown in FIG. 3, the printer port 23 may comprise a Centronic or other suitable printer port for the connection of standard printers to the power console 12. The mass storage output 24 may comprise one or more mass storage output connectors such as standard USB connectors connectible with USB enabled printers and/or mass storage devices such as digital film card readers. The accessory power output 26 may comprise an accessory power outlet for connecting the power console 12 to peripheral devices to be powered by the power console for use with the intraoperative neural monitoring system 10. The audio/video output 28 may comprise an audio output jack 28a providing, for example, an audio line level 1Vp-p output to external devices, and/or a video output connector 28b, such as a standard VGA 15 pin connector, connectible with an external VGA monitor for remote viewing of touch screen displays or for external video recording. The power console 12 may also include a connector 41 for connection with audio headphones to permit private listening or for connection with a keyboard. A mode switch 42 may be provided on the power console 12 to allow factory or custom settings to be selected for the intraoperative neural monitoring system 10. The power input 20, printer port 23, mass storage output 24, accessory power output 26, audio/video output 28, switch 34, fuse access 35, patient interface connector 36, auxiliary connector 37, hand switch connector 38, muting detector connectors 39, ground element 40 and mode switch 42 may be disposed on the back of the power console 12, which is shown in FIG. 3, but could be disposed at any suitable locations on the power console.

Figure 4:
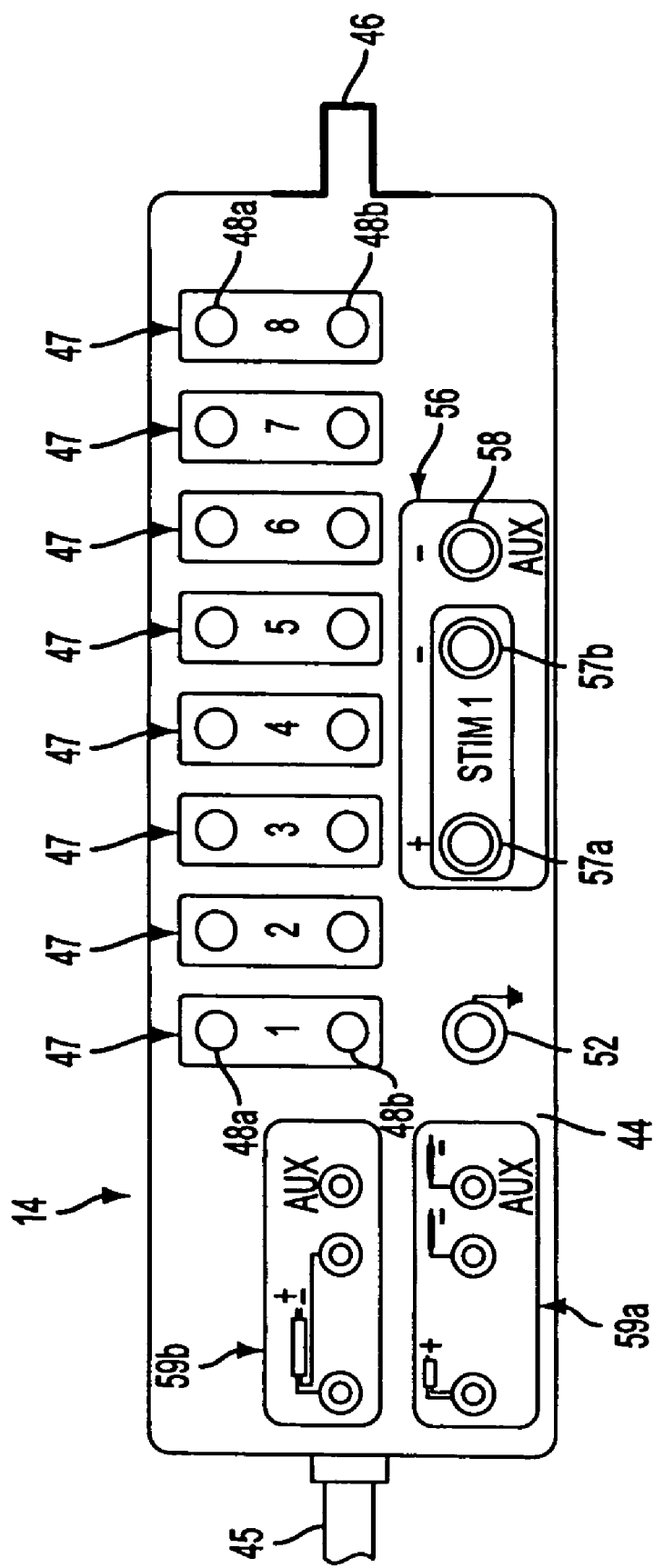
FIG. 4 is a broken plan view of a patient interface unit of the intraoperative neural monitoring system for delivering Stim 1 electrical stimulation.
Figure 5:
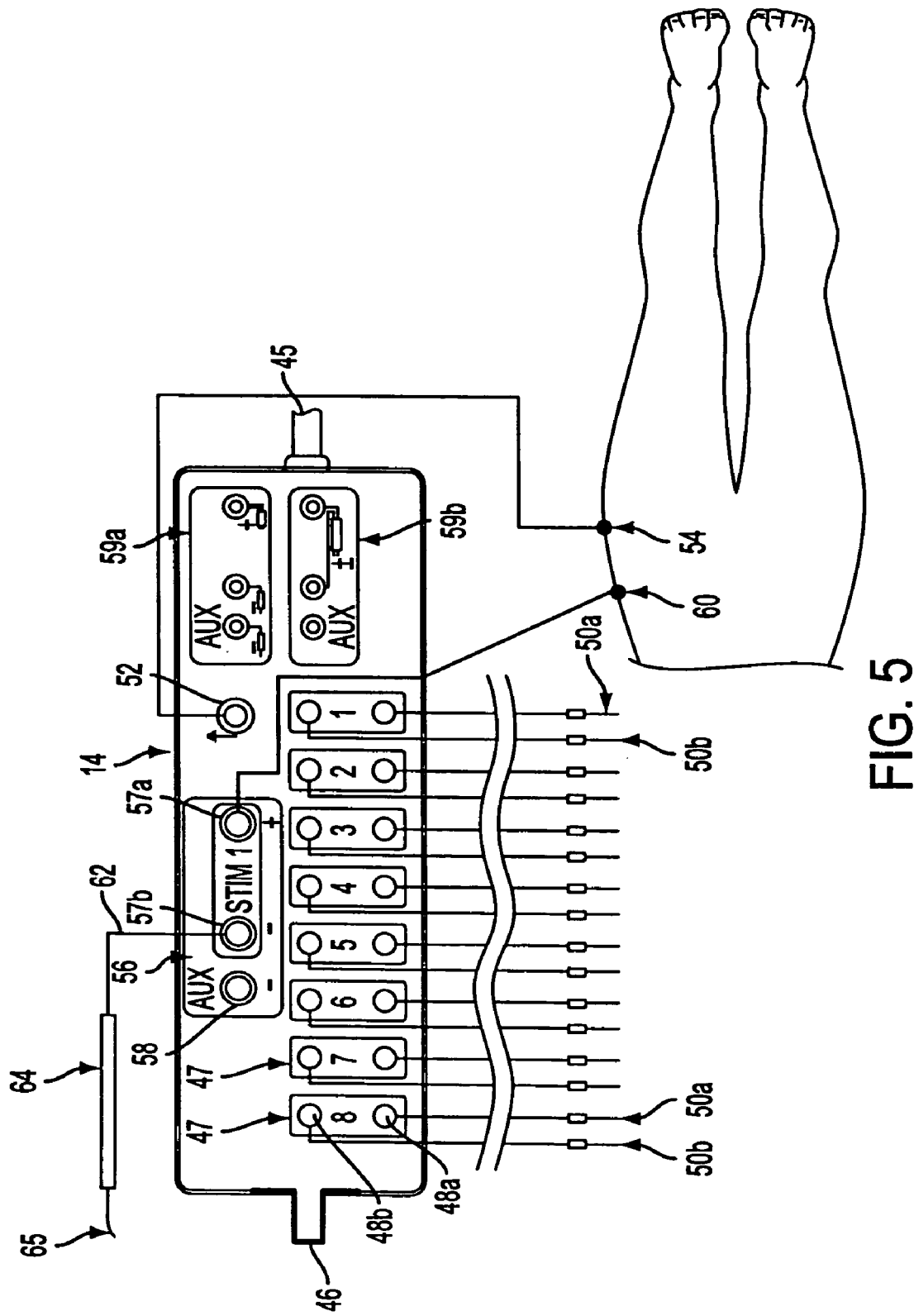
FIG. 5 is a broken plan view depicting a representative set-up arrangement for the patient interface unit for monopolar electrical stimulation of a patient, with the patient's body not being shown to scale with respect to the patient interface unit.
Figure 6:
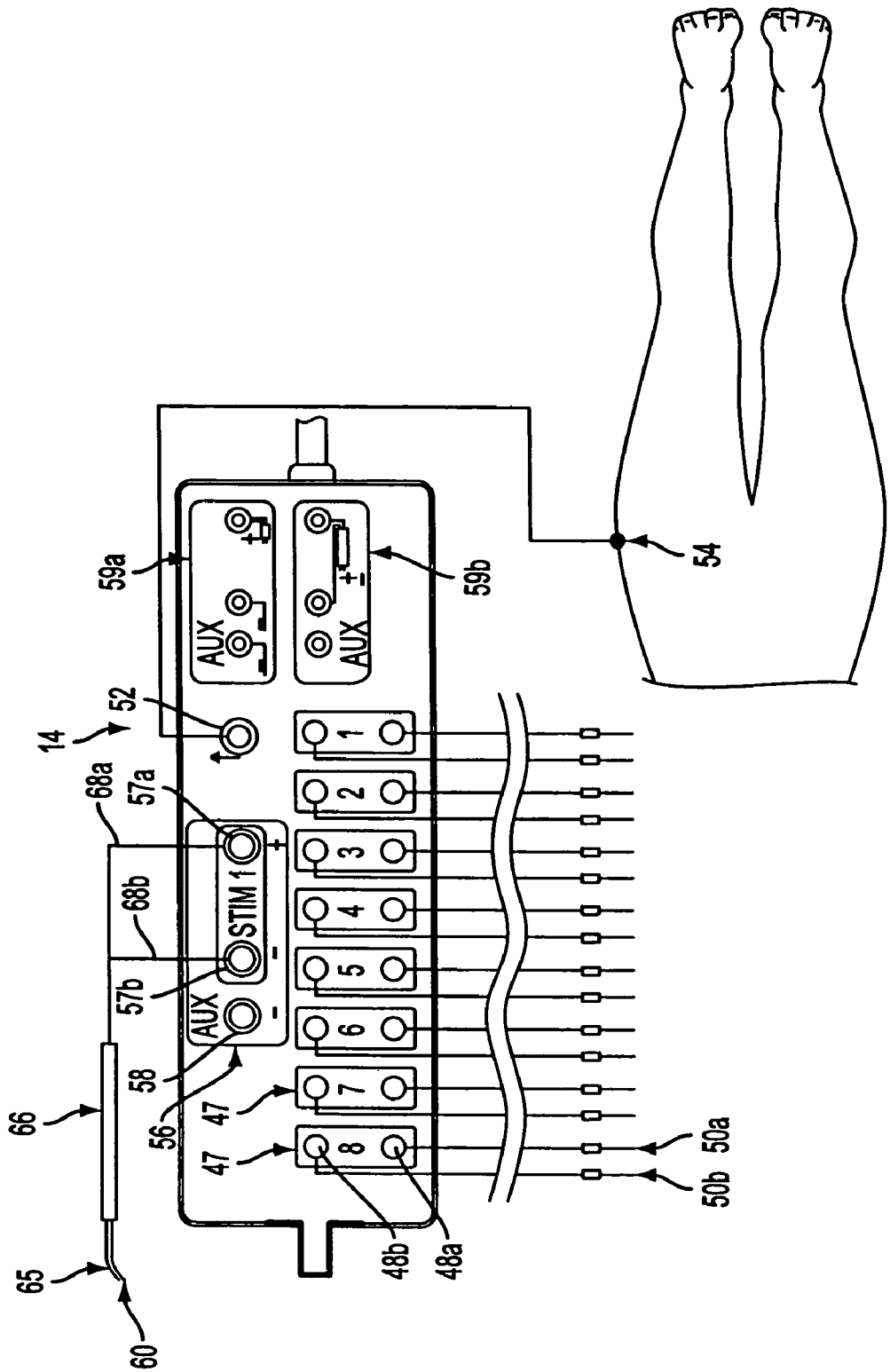
FIG. 6 is a broken plan view depicting a representative set-up arrangement for the patient interface unit for bipolar electrical stimulation of a patient, with the patient's body not being shown to scale with respect to the patient interface unit.

The patient interface unit 14 is illustrated in FIG. 4 and comprises a housing or enclosure 44 connected to one end of an electrical cable 45, the opposite end of which carries a connector connectible with the patient interface connector 36. The cable 45 establishes electrical connection between the power console 12 and the patient interface unit 14, and electric power from the power console is supplied to the patient interface unit via the cable 45. A clip 46 may be provided on the housing 44 allowing the patient interface unit 14 to be attached to a bed sheet or another appropriate object to be out of the way when used during an operative procedure. The patient interface unit 14 includes a plurality of monitoring channels 47, preferably eight monitoring channels 47, each having two monitoring or recording electrode inputs or connectors (positive and negative) 48a and 48b respectively connectible with a corresponding pair of monitoring or recording electrodes (positive and negative) 50a and 50b as shown in FIGS. 5 and 6. The monitoring electrode inputs 48a and 48b may each comprise a jack or other suitable connector for electrical connection with a connector carried at one end of a wire leading from the corresponding monitoring electrode 50a, 50b. The connectors and/or wires of each pair of monitoring electrodes 50a, 50b are preferably color coded to the corresponding monitoring channel 47. The monitoring electrodes 50a, 50b may comprise electrically conductive needles or other suitable structure for insertion in a muscle at which EMG activity is to be monitored. The monitoring electrodes detect EMG activity in the muscles, and signals corresponding to the detected EMG activity are transmitted to the power console 12 via the patient interface unit 14 and are displayed as waveforms on the touch screen 30 of the power console as explained further below. A single ground connector 52 is provided on the patient interface unit 14 for all monitoring channels 47. The ground connector 52 may comprise a jack or other suitable connector for electrical connection with a connector carried at one end of a wire leading from a ground electrode 54 as shown in FIGS. 5 and 6. Preferably, the wire and/or connector of the ground electrode 54 are color coded to the ground connector 52. Depending on the intended location for the ground electrode 54, the ground electrode 54 may comprise a conductive needle or any other suitable structure.

The patient interface unit 14 includes a probe interface 56 for connection of a monopolar or bipolar stimulating probe to the patient interface unit. The probe interface 56 comprises connectors 57a (positive) and 57b (negative) as well as an auxiliary connector 58 (negative). Each probe interface connector 57a, 57b and 58 may comprise a jack or other suitable electrical connector. Two connection diagrams are provided on the housing 44, one connection diagram 59a diagrammatically depicting connection of a monopolar stimulating probe to the probe interface 56 for monopolar Stim 1 electrical stimulation and the other connection diagram 59b diagrammatically depicting connection of a bipolar stimulating probe to the probe interface for bipolar Stim 1 electrical stimulation.

FIG. 5 depicts a representative set-up arrangement for the patient interface unit 14 for monopolar Stim 1 stimulation in accordance with connection diagram 59a. A connector carried at one end of a wire leading from a return electrode or anode 60 (positive) is electrically connected with the connector 57a (positive) of the probe interface 56, and the return electrode 60 is applied to the patient at an appropriate anatomical location. Depending on the intended location for the return electrode 60, the return electrode 60 may comprise single or multiple conductive needles or any other suitable structure for penetrating anatomical tissue. Preferably, the wire and/or connector of the return electrode 60 are color coded to the connector 57a. A connector at the end of a connection cable 62 leading from a monopolar stimulating probe 64 is electrically connected to the connector 57b (negative), and the connector and/or connection cable of the monopolar stimulating probe 64 are preferably color coded to the connector 57b. The probe 64 has a tip comprising an output electrode or cathode 65 (negative). The ground electrode 54 is connected to the ground connector 52, and the ground electrode 54 is applied to a non-intervated, electrically neutral anatomical area of the patient. Pairs of monitoring electrodes 50a and 50b are connected to the monitoring electrode inputs 48a and 48b, respectively, of a desired number of monitoring channels 47 for which monitoring is to be conducted. The monitoring electrodes 50a and 50b are inserted in anatomical tissue so as to detect EMG activity in selected muscle as explained further below. Stim 1 electrical stimulation is delivered to the probe 64 from the patient interface unit 14, and the output electrode or cathode 65 delivers monopolar Stim 1 electrical stimulation to anatomical tissue contacted with the output electrode 65 of the probe. Electrical current delivered via the monopolar stimulating probe 64 flows to the distant return electrode 60, while essentially spreading in all directions from the output electrode 65 at the tip of the probe. The auxiliary connector 58 can be used if more than one monopolar stimulating probe is required to be used during the operative procedure, with both connectors 57b and 58 being controlled by the same stimulation settings selected for Stim 1 electrical stimulation as explained further below.

FIG. 6 depicts a representative set-up arrangement for the patient interface unit 14 for bipoloar Stim 1 electrical stimulation in accordance with connection diagram 59b using a bipolar stimulating probe 66. The connection cable leading from the bipolar stimulating probe 66 includes wires 68a and 68b leading from a return electrode or anode 60 (positive) and an output electrode or cathode 65 (negative), respectively, disposed in close proximity to one another at the tip of the probe 66. A connector at the end of wire 68a is electrically connected with the connector 57a, and a connector at the end of wire 68b is electrically connected with the connector 57b. Preferably, the connectors and/or wires of the probe 66 are color coded to the corresponding connectors 57a and 57b. The monitoring electrodes 50a and 50b and the ground electrode 54 are connected to the patient interface unit 14 and applied to the patient in the same manner as described above for monopolar Stim 1 stimulation. Stim 1 electrical stimulation is delivered to the probe 66 from the patient interface unit 14 and, when the tip of the bipolar stimulating probe 66 is placed in contact with anatomical tissue, current flows through the tissue directly from the output electrode 65 to the return electrode 60 at the tip of the probe.

Monopolar and bipolar stimulating probes may be used to provide electrical stimulation in the area of a nerve. If the stimulation is applied at or reasonably near the nerve, the stimulation signal is applied to the nerve and is transmitted through the nerve to excite the related muscle. Excitement of the muscle causes an electrical impulse (EMG) to be generated within the muscle, the impulse being detected by the monitoring electrodes which have been placed in the muscle. Monitoring EMG activity evoked in response to stimulation applied via stimulating probes connected with the patient interface unit 14 allows the location and/or integrity of nerves to be ascertained. The intraoperative neural monitoring system 10 also allows EMG activity at the monitoring electrodes to be continuously monitored even while no electrical stimulation is being applied and nerves are not being manipulated by the surgeon. Continuous EMG monitoring provides at rest or baseline EMG parameters which facilitate identification of potentially significant intraoperative changes in monitored EMG activity.

It should be appreciated that color coding of the patent interface unit to monitoring and ground electrodes and to stimulating probes may be accomplished in various ways. Also, the term "wire" as used herein is intended to encompass a single wire or a plurality of wires. U.S. Pat. No. 6,334,068 B1 to Hacker is incorporated herein by reference as providing teachings pertinent to an understanding of the design and operation of the power console 12 and patient interface unit 14 as well as stimulation via monopolar and bipolar stimulating probes and EMG monitoring via monitoring electrodes. It should also be appreciated that the term "nerve" as used herein is intended to encompass various nerves and nerve roots.

Figure 7:
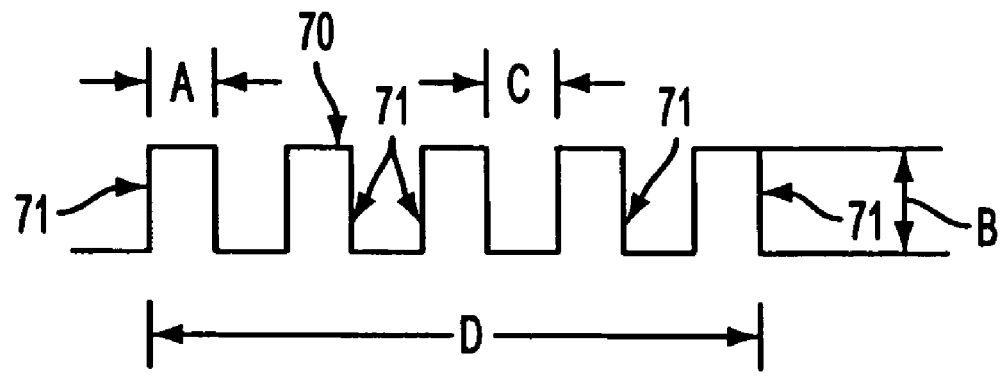
FIG. 7 illustrates a waveform representing monophasic electrical stimulation delivered by the patient interface unit.

The stimulation delivered from the patient interface unit 14 to the monopolar or bipolar stimulating probe 64, 66 is a first form of electrical stimulation or Stim 1 electrical stimulation. Stim 1 electrical stimulation is continuous monophasic electrical stimulation comprising continuous constant current (DC) square wave pulses. A waveform 70 representing Stim 1 electrical stimulation is shown in FIG. 7. Each pulse 71 of waveform 70 has a duration or pulse width A (time) and a level B (current amplitude), with there being a delay C (time) between successive pulses. The pulses 71 are delivered at a rate D (pulses/second). The pulses 71 are all positive, being delivered from cathode to anode. The intraoperative neural monitoring system 10 is designed to provide Stim 1 electrical stimulation that may be selected to have a duration or pulse width A in the range of 50 to 250 microseconds and preferably 50, 100, 150, 200 or 250 microseconds, a level or current amplitude B ranging from 0 to 30 mA, max 120V compliance, and a rate D in the range of 1 to 10 pulses/second and preferably 1, 5 or 10 pulses/second, with the delay C being dependent on the selected duration and rate. The patient interface unit 14 may be considered a low current stimulator of the intraoperative neural monitoring system 10. As explained further below, control options on the touch screen 30 are used to select and/or adjust various parameters or settings for Stim 1 stimulation including the duration A, level B and rate D. Once a stimulating probe is connected to the patient interface unit 14 and its tip is brought into contact with anatomical tissue or a medical device in contact with the anatomical tissue, the electrical stimulus is delivered continuously for as long as the probe tip is in physical contact with the tissue or medical device.

Figure 8:
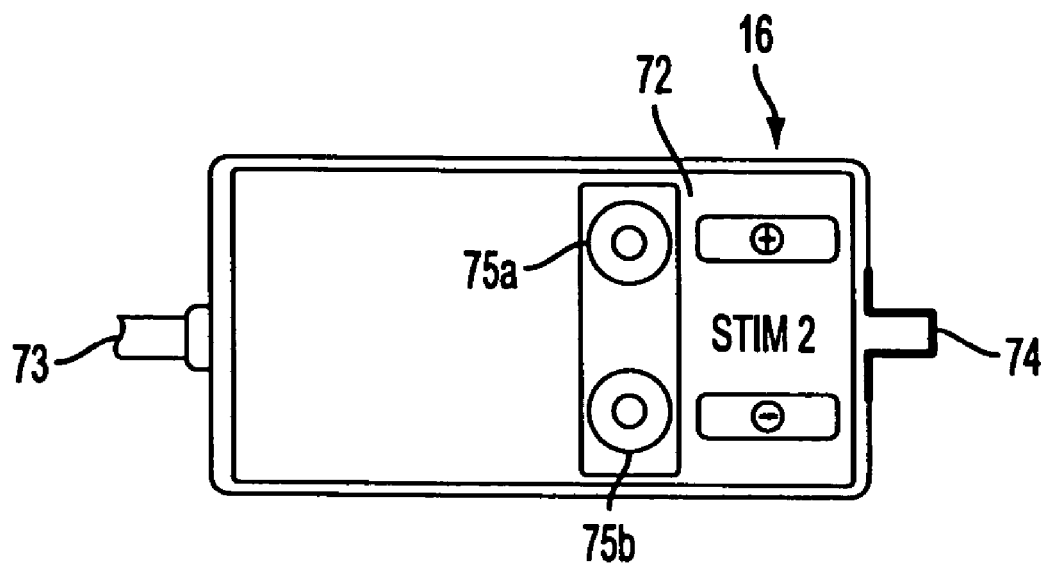
FIG. 8 is a broken plan view of a stimulator of the intraoperative neural monitoring system for delivering Stim 2 electrical stimulation.

The stimulator 16 is illustrated in FIG. 8 and comprises a housing or enclosure 72 connected to one end of an electrical cable 73, the opposite end of which carries a connector connectible with the auxiliary connector 37 on the power console 12. The cable 73 establishes electrical connection between the power console 12 and the stimulator 16, and electric power from the power console is supplied to the stimulator via the cable 73. A clip 74 may be provided on the housing 72 allowing the stimulator 16 to be attached to a bed sheet or another appropriate object to be out of the way when used during an operative procedure. The stimulator 16 includes two stimulating electrode inputs or connectors 75a and 75b identified by corresponding indicia on the housing 72 as anode (positive) and cathode (negative), respectively. The stimulating electrode inputs 75a and 75b may each comprise a jack or other suitable electrical connector and are respectively connectable with connectors carried at the ends of wires leading from a pair of stimulating electrodes 76a and 76b as depicted in FIG. 9.

Figure 9:
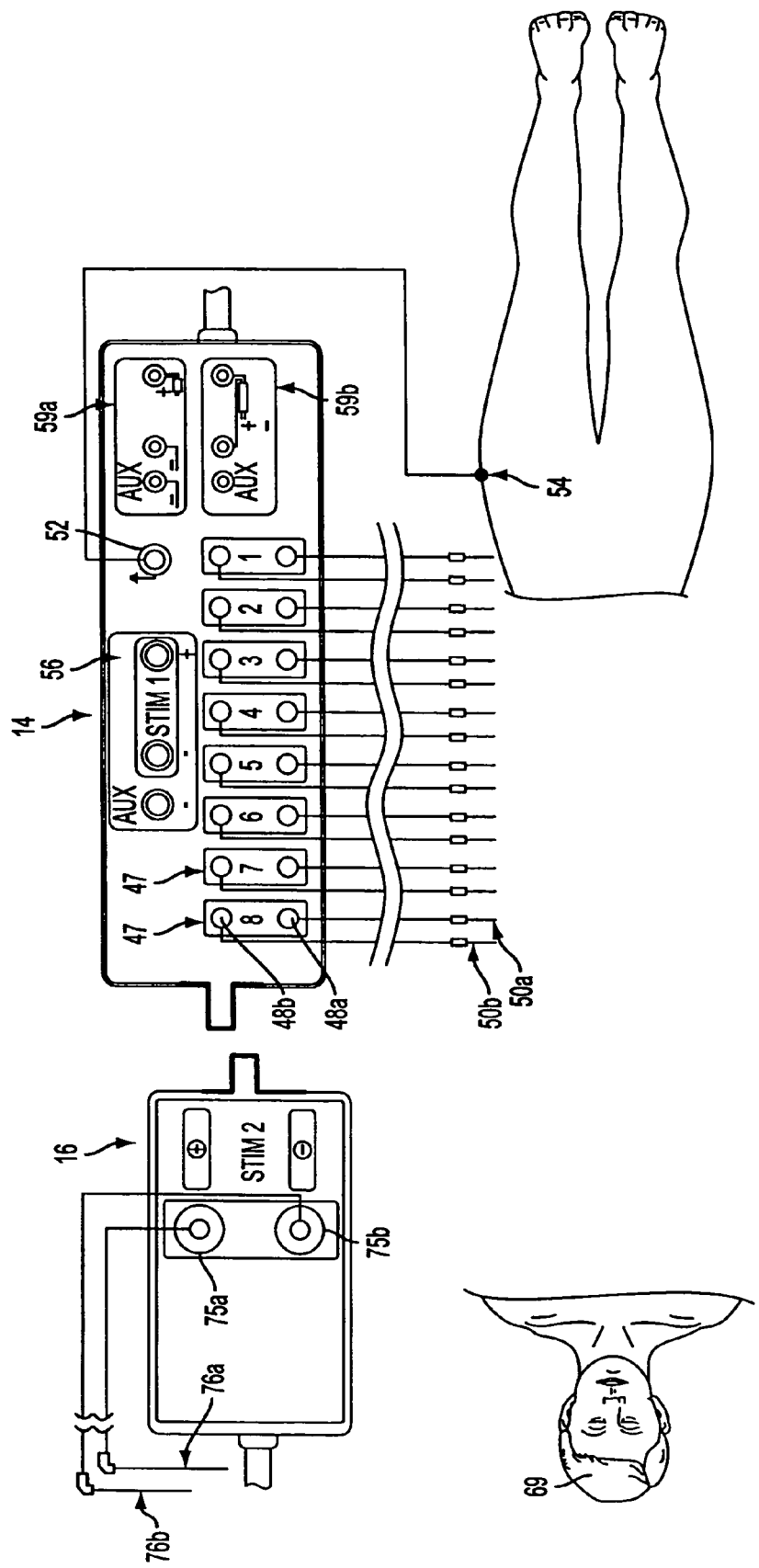
FIG. 9 is a broken plan view depicting a representative set-up arrangement for the simulator, with the patient's body not being shown to scale with respect to the stimulator.
Figure 10:
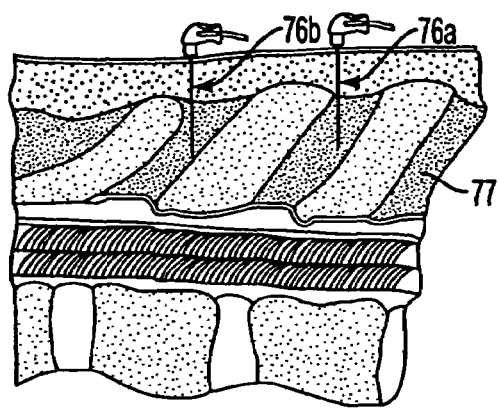
FIG. 10 is a broken view, partly in section, depicting a representative application of the stimulating electrodes for the stimulator in which the stimulating electrodes are applied to the spine for spinal cord stimulation.

FIG. 9 illustrates a representative set-up arrangement for the stimulator 16 for Stim 2 electrical stimulation. The connector carried at the end of the wire leading from the stimulating return electrode or anode 76a (positive) is connected to the stimulating electrode input 75a (positive), and the connector carried at the end of the wire leading from the stimulating output electrode or cathode 76b (negative) is connected to the stimulating electrode input 75b (negative). The connectors and/or wires of the stimulating electrodes 76a and 76b are preferably color coded to the corresponding stimulating electrode inputs 75a and 76b as described above. The stimulating electrodes 76a and 76b are applied to anatomical tissue to be stimulated and, depending on the intended anatomical location for the stimulating electrodes, the stimulating electrodes may be configured as low impedance needles, insulated or uninsulated K wires, or any other suitable configuration for penetrating anatomical tissue. For transcranial electrical stimulation, as represented by FIG. 9, the stimulating electrodes 76a and 76b may be placed in the scalp 69 at spaced anatomical locations suitable to effect stimulation of the left and right motor cortex. For example, the stimulating electrode 76a may be placed subdermally in the scalp at the vertex with the stimulating electrode 76b placed subdermally in the scalp at a location 7 cm lateral to stimulating electrode 76a. For direct spinal cord stimulation, the stimulating electrodes 76a and 76b may be placed through the skin of the patient's back and into the interspinous ligament 77 at spaced locations along the spine as depicted in FIG. 10. The stimulating electrodes 76a, 76b may be placed between the interspinous processes to a posterior depth for posterior spinal cord stimulation or may be placed deeper into the bone to an anterior depth for anterior spinal cord stimulation. The patient interface unit 14 is arranged with the ground electrode 54 connected and applied as described above for Stim 1 stimulation. Pairs of monitoring electrodes 50a, 50b for a desired number of monitoring channels 47 are connected to the patient interface unit 14 and disposed in anatomical tissue to detect EMG activity (compound muscle action potential) in a muscle or muscles affected by the Stim 2 electrical stimulation delivered by the stimulator 16. Stim 2 electrical stimulation is delivered to the stimulating output electrode or cathode and flows through the anatomical tissue to the stimulating return electrode or anode. As described further below, depending on the polarity or phase selected for Stim 2 electrical stimulation, the stimulating electrodes 76a, 76b may each function as the output electrode or cathode. For positive phase Stim 2 stimulation, the stimulating electrode 76b functions as the output electrode or cathode with the stimulating electrode 76a functioning as the return electrode or anode. For negative phase Stim 2 stimulation, the stimulating electrode 76a functions as the output electrode or cathode with the stimulating electrode 76b functioning as the return electrode or anode.

Figure 11:
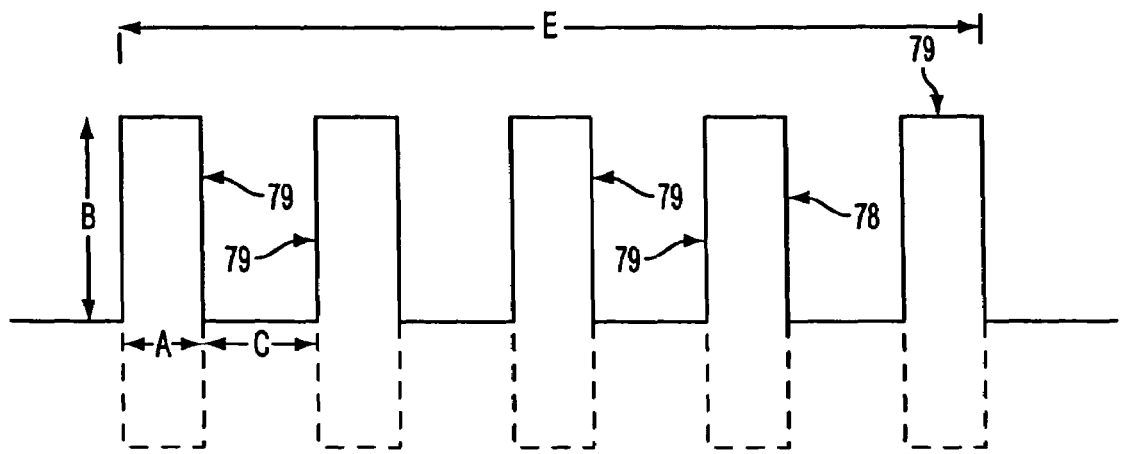
FIG. 11 depicts a waveform representing a complete cycle of monophasic electrical stimulation delivered by the stimulator.

The stimulation delivered to the stimulating output electrode 76a or 76b from the stimulator 16 is a second form of electrical stimulation or Stim 2 electrical stimulation. Stim 2 electrical stimulation is delivered in a monophasic or biphasic mode as a finite or complete cycle of electrical stimulation comprising a finite number of constant current (DC) square wave pulses. A waveform 78 representing a single complete cycle of monophasic Stim 2 electrical stimulation is shown in FIG. 11. Waveform 78 comprises a single group of pulses 79, each pulse 79 having a duration or pulse width A (time) and a level B (current amplitude). The group of pulses contains a preselected number or repetition E of pulses 79, with there being a delay C (time) between successive pulses. The complete cycle of monophasic Stim 2 stimulation depicted by way of example in FIG. 11 is shown as having five pulses 79. The pulses 79 are of the same phase and may be selected as being all positive (+) phase pulses, i.e. delivered from stimulating electrode 76b to stimulating electrode 76a in a positive monophasic mode as shown in solid lines in FIG. 11, or as all negative (−) phase pulses, i.e. delivered from stimulating electrode 76a to stimulating electrode 76b in a negative monophasic mode as shown in dotted lines in FIG. 11. Accordingly, positive pulses 79 are delivered in a first direction or polarity from the output stimulating electrode 76b to the return stimulating electrode 76a. Negative pulses 79 are delivered in a second direction or polarity from the stimulating electrode 76a, which then functions as the output stimulating electrode or cathode, to the stimulating electrode 76b, which then functions as the return stimulating electrode or anode. The waveform 78 also illustrates the negative phase pulses selected as being of less current amplitude than the positive phase pulses.

Figure 12:
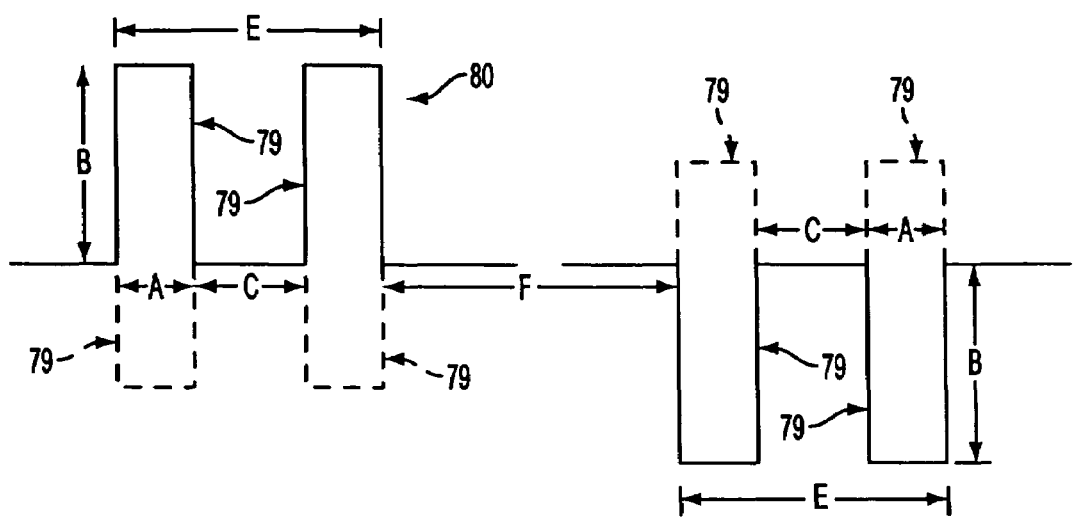
FIG. 12 illustrates a waveform representing a complete cycle of biphasic electrical stimulation delivered by the stimulator.

A waveform 80 representing a single complete cycle of biphasic Stim 2 electrical stimulation is shown in FIG. 12. Waveform 80 comprises two groups of pulses 79, with the second group of pulses 79 being separated from the first group of pulses 79 by an interval F (time). Each pulse 79 has a duration or pulse width A (time) and a level B (current amplitude), with there being a delay C (time) between successive pulses of each group. Each group of pulses contains a preselected number or repetition E of pulses 79, and the repetition E is the same for each group of pulses. As an example, the complete cycle of biphasic Stim 2 stimulation depicted in FIG. 12 has a total of four pulses, i.e. two pulses in each group. The groups of pulses are of different or opposite phase, one group of pulses 79 being positive phase pulses and the other group of pulses 79 being negative phase pulses. FIG. 12 illustrates in solid lines a first group of positive phase pulses 79 followed by a second group of negative phase pulses 79 in a positive leading biphasic mode. However, as shown in dotted lines in FIG. 12, a first group of negative phase pulses can be followed by a second group of positive phase pulses in a negative leading biphasic mode. The current amplitude B for the positive pulses is the same as the current amplitude of the negative pulses (equal biphasic). FIG. 12 depicts the pulses of the dotted line waveform as being selected to have a level or current amplitude less than that of the pulses of the solid line waveform.

As explained further below, initiating delivery of Stim 2 stimulation from the stimulator 16 requires actuation by the user completing performance of a multi-step manual actuation procedure with an activator for the stimulator 16. In response to a multi-step manual actuation procedure completed by the user to start delivery of a Stim 2 stimulation cycle, the stimulator 16 delivers a complete cycle of Stim 2 stimulation in accordance with parameters or settings preselected by the user for the Stim 2 stimulation. The intraoperative neural monitoring system 10 is designed to provide Stim 2 electrical stimulation that may be selected by the user to have a duration A in the range of 100 to 500 microseconds and preferably 100, 250 or 500 microseconds, a level B ranging from 0–200 mA, max 750V compliance, a delay C in the range of 2 to 4 milliseconds and preferably 2, 3 or 4 milliseconds, and a repetition E of 1–8 pulses. For biphasic Stim 2 electrical stimulation, the interval F is a fixed, predetermined interval, preferably about 2 seconds. The stimulator 16 may be considered a high current stimulator of the intraoperative neural monitoring system 10. As explained further below, the touch screen 30 is used to select and/or adjust various parameters or settings for Stim 2 electrical stimulation including mode (monophasic or biphasic), duration A, level B, delay C and repetition E. Once actuated, the stimulator 16 will deliver the complete cycle of Stim 2 electrical stimulation, with subsequent cycles of Stim 2 electrical stimulation being delivered by reactuation the stimulator.

Figure 13:
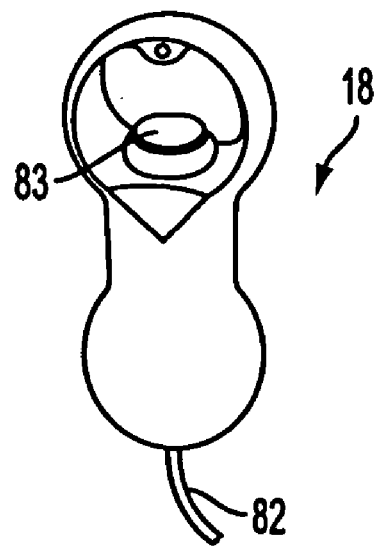
FIG. 13 is a broken perspective view of a hand switch of the intraoperative neural monitoring system for activating delivery of electrical stimulation from the stimulator.

Actuation for Stim 2 stimulation may be accomplished via a button or other control option of the touch screen 30 serving as an activator for actuating stimulator 16 as described below or remotely via the hand switch 18, illustrated in FIG. 13, serving as the activator. The hand switch 18 is connected to an electrical cable 82 carrying an electrical connector (not shown) that connects to the hand switch connector 38 on the power console 12. The hand switch 18 may be selected by the user as the activator for the stimulator 16 and includes an activation button 83 that is pressed twice to complete the multi-step manual actuation procedure and start delivery of Stim 2 stimulation from the stimulator 16. Pressing the button 83 once causes a dialog box to open on the touch screen 30. Pressing the button 83 a second time activates an acceptance button of the dialog box and effects delivery of a complete cycle of Stim 2 electrical stimulation from the stimulator 16. Actuation can be canceled by pressing a "cancel" button of the dialog box prior to pressing the button 83 the second time. The button 83 must be pressed the second time within a predetermined time interval following the first press on button 83, and a preferred interval is about 0.1 to about 4.0 seconds after the first press. If the button 83 is pressed for the second time sooner than the predetermined time interval, the second press does not register and the button may be pressed again within the predetermined time interval. If the button 83 is pressed after the predetermined time interval, the power console 12 will reset and the button 83 will again have to be pressed two consecutive times to effect delivery of Stim 2 stimulation. Two-step actuation as required by the hand switch 18 thusly ensures that Stim 2 electrical stimulation is definitively selected and confirmed prior to delivery of the electrical stimulus to the patient.

Figure 14:
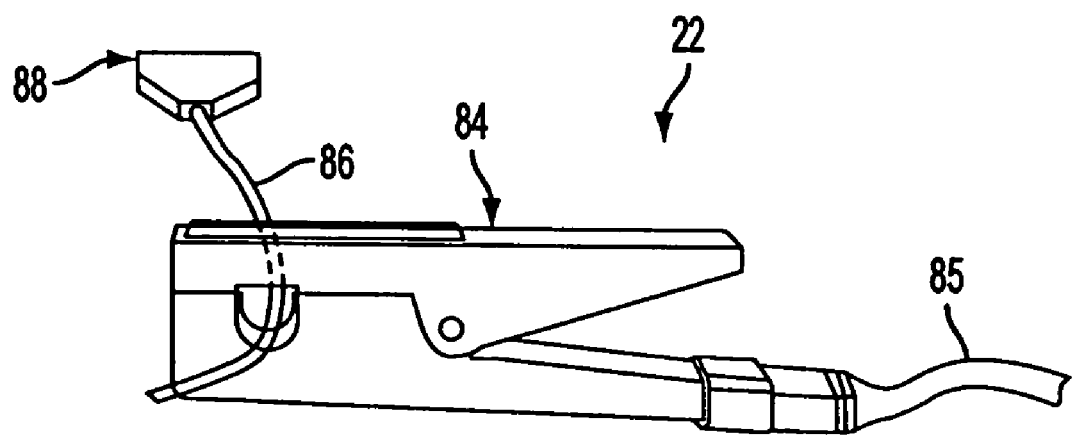
FIG. 14 is a broken perspective view illustrating use of a muting detector of the intraoperative neural monitoring system.

During many surgical procedures, an electrified medical instrument such as an electrosurgical or electrocautery instrument may be used as a surgical knife, to assist in hemostasis or for other purposes. High frequency (HF) energy generated by an electrified instrument used during an operative procedure may be transmitted through the patient and picked up by the monitoring electrodes, such that the HF energy may be amplified by the intraoperative neural monitoring system 10 to disturbing volume levels. The one or more muting detectors 22 may be used in the intraoperative neural monitoring system 10 to detect when an electrified instrument or instruments is/are in use which may cause interference with EMG monitoring. A muting detector 22 is depicted in FIG. 14 and comprises a clamp 84 connected to one end of an electrical cable 85, the opposite end of which carries an electrical connector (not shown) that connects with one of the muting detector connectors 39 on the power console 12. The clamp 84 clamps onto the active cable 86 of an electrified medical instrument 88 which may generate HF energy through the patient that may be picked up by the monitoring electrodes. The clamp 84 may be clamped onto the active cable 86 by inserting the active cable between pivotal jaws of the clamp. The instrument 88 may be an electrosurgical or electrocautery instrument, an ultrasonic debulking instrument, e.g. CUSA, an electric drill or any other instrument that may generate interfering signals. The muting detector 22 senses when current flows through the active cable 86, and auditory and visual output for EMG monitoring are disabled while current flow through the active cable is sensed. The active cables of more than one instrument may be clamped between the jaws of the clamp 84 at the same time. Muting sensitivity can be adjusted via the muting detector connectors 39, which are individually preset to represent varying graduated levels of muting gain. The muting detector connectors 39 may be assigned successively increasing numbers corresponding to successively increasing levels of muting detection sensitivity. Preferably, an intermediate level of muting detection sensitivity assigned to one of the muting detector connectors 39 corresponds to the typical gain value for muting detection. Depending on conditions in the operating room and/or the amount of detection desired for a particular electrified instrument 88, the connector of the muting detector 22 can be connected with the muting detector connector 39 of appropriate muting detection sensitivity.

Figure 15:
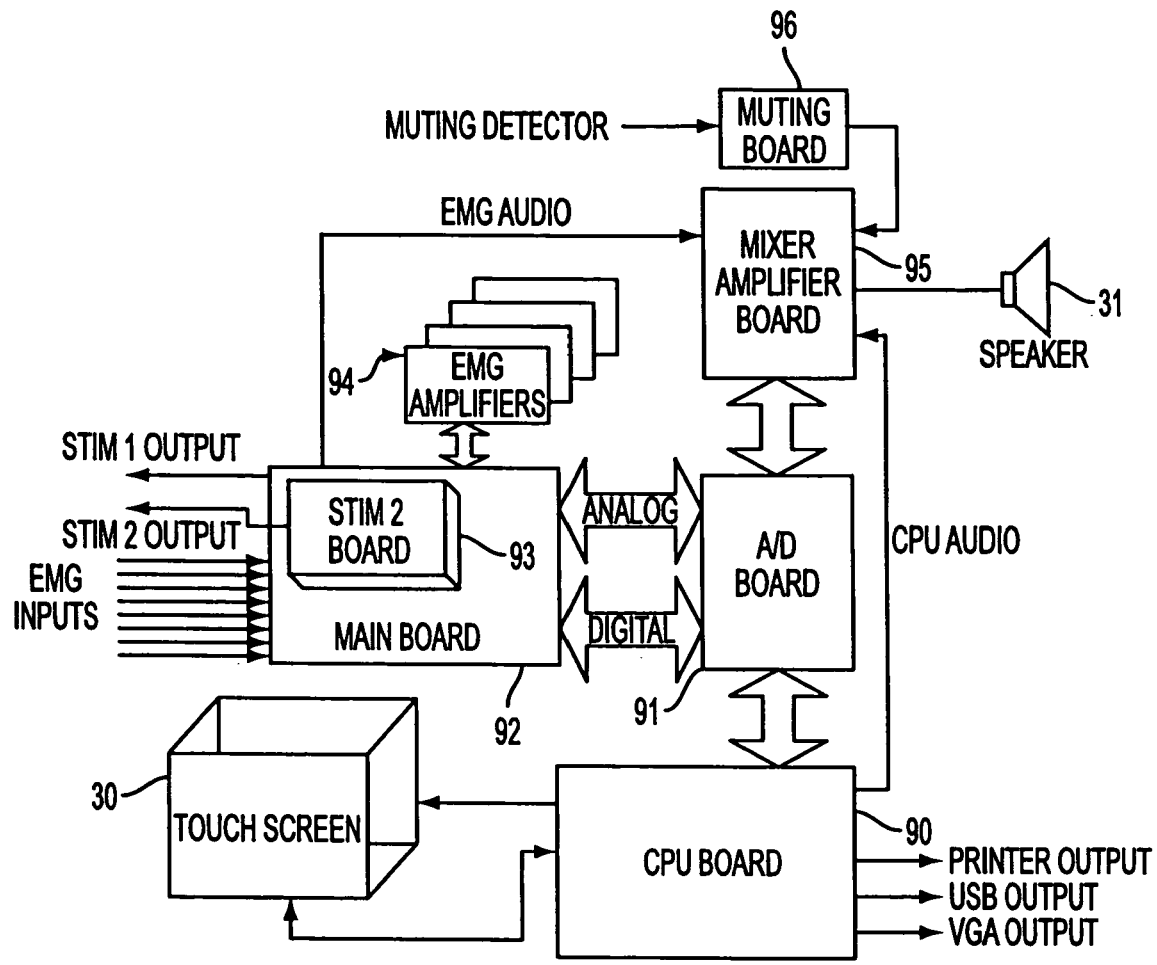
FIG. 15 is a diagram depicting a hardware configuration for the intraoperative neural monitoring system.

FIG. 15 depicts a representative hardware configuration for the intraoperative neural monitoring system 10. The intraoperative neural monitoring system 10 comprises a central processing unit (CPU) 90 interfacing with touch screen 30 and with an A/D (analog/digital) circuit board 91, a main circuit board 92 in electrical communication with the A/D board, a secondary or Stim 2 circuit board 93 controlled via the main board 92, EMG amplifiers 94 interfacing with the main board, a mixer amplifier circuit board 95 interfacing with the CPU and main board, and a muting circuit board 96 interfacing with the mixer amplifier board. The CPU 90 may provide outputs such as the printer port, mass storage output and audio/video output for various external devices as shown in FIG. 15. The touch screen 30 interfaces with the CPU 90 via a touch screen controller and produces an analog voltage proportional to the coordinates of a depressed area on the touch screen. The touch screen controller scans for touch screen presses and relays them to the CPU 90 via a communications port. The AND board 91 comprises analog and digital inputs and outputs, and both analog and digital signals are routed between the AND board and the main board 92. The main board 92 provides the output for Stim 1 electrical stimulation, and the secondary or Stim 2 board 93 provides the output for Stim 2 electrical stimulation. The main board 92 receives EMG signal inputs from the monitoring electrodes, the EMG inputs being amplified by the EMG amplifiers 94 and further processed by the mixer amplifier board 95. The mixer amplifier board 95 mixes, combines and amplifies audio signals to speaker 31, provides volume control, and generates voice messages. The mixer amplifier board 95 accepts a muting signal from the muting board 96 and mutes the audio outputs to speaker 31 when the muting signal is excessive.

Figure 16:
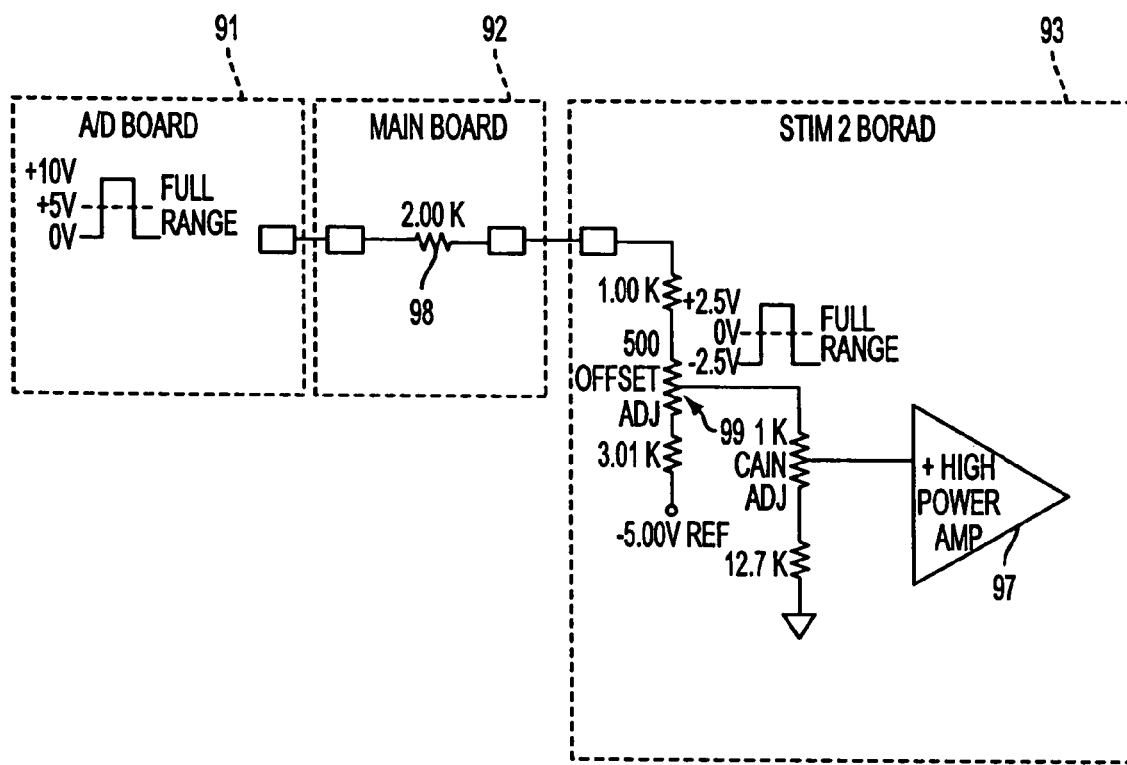
FIG. 16 depicts an input control voltage circuit for a high power amplifier used to generate Stim 2 electrical stimulation delivered from the stimulator.

As shown in FIG. 16, The Stim 2 board 93 includes a high power amplifier 97 providing a voltage controlled current source. The control voltage for the high power amplifier 97 is provided from the main board 92 through the A/D board 91 under control of system software. The control voltage is an analog image of the desired output for Stim 2 electrical stimulation. It is routed to the high power amplifier 97 through a resistor of the main board 92. The 0 to 10V range of the A/D board 91 is halved to 0 to +5V by a resistive divider network of the Stim 2 board 93, then level shifted to +/−2.5V via a −5V reference powered by a 12V system power supply. Comparators may be used to carry out logic functions associated with converting incoming 5V logic to 12V logic required by the circuits being controlled.

Figure 17:
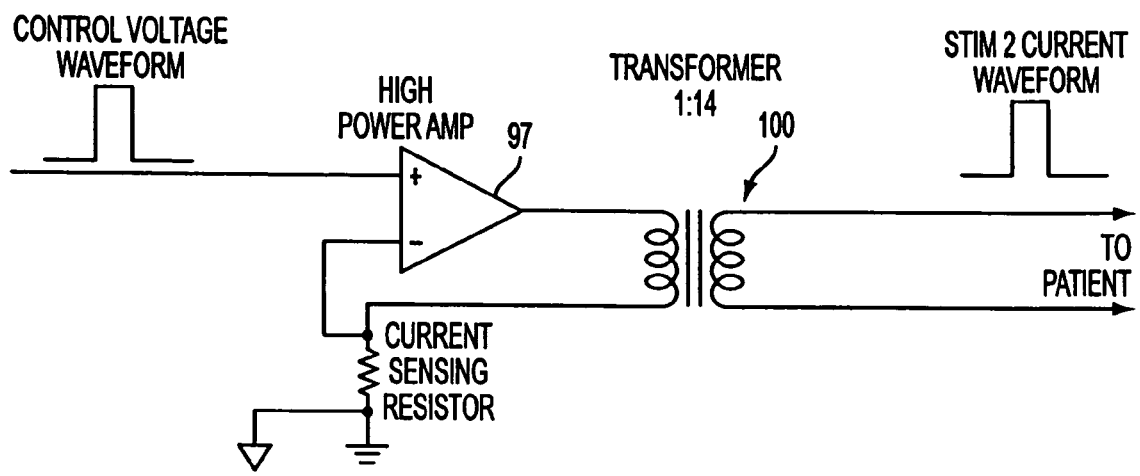
FIG. 17 illustrates the delivery of controlled current from the high power amplifier through a transformer.
Figure 18:
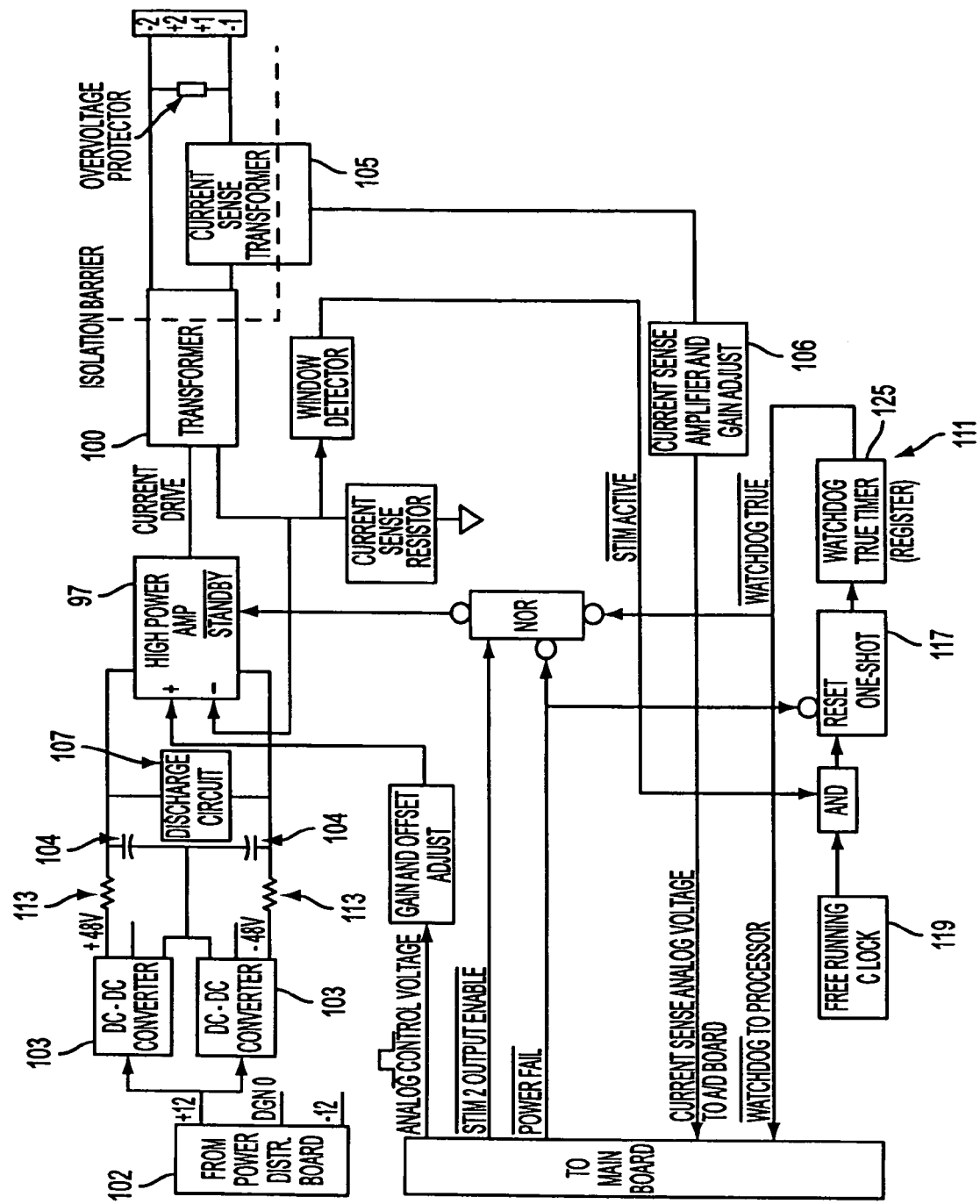
FIG. 18 is a block diagram depicting the generation of positive and negative phase electrical stimulation pulses for delivery from the stimulator as monophasic or automatic biphasic electrical stimulation.

From the high power amplifier 97, controlled current is provided to the primary winding of a transformer 100 as shown in FIG. 17. Controlled current is provided from the high power amplifier 97 to the transformer 100 via a current sensing resistor feeding back to the negative input to the high power amplifier 97. Current output from the transformer 100 is delivered from the stimulator 16 as Stim 2 electrical stimulation. Trains of 1 to 8 positive or negative phase pulses optionally followed by an equal number of pulses of opposite polarity can be generated in a single complete cycle of Stim 2 stimulation. FIG. 18 illustrates a block diagram depicting generation of positive and negative phase Stim 2 electrical stimulation via the high power amplifier 97 and the transformer 100. FIG. 18 depicts the 12V system power supply 102 which powers two switching +/−24V DC/DC converters 103 that charge energy storage capacitors 104, respectively, providing energy for the Stim 2 pulses. The outputs of each converter 103 are stacked so as to generate +/−48V rails. One energy storage capacitor 104 provides positive phase pulses, and the other energy storage capacitor 104 provides negative phase pulses. Delivered Stim 2 current information is provided to the CPU 90 via a current sense transformer and current sense amplifier, which provides a scaled input to an analog input channel of the A/D board as shown in FIG. 18.

Figure 19:
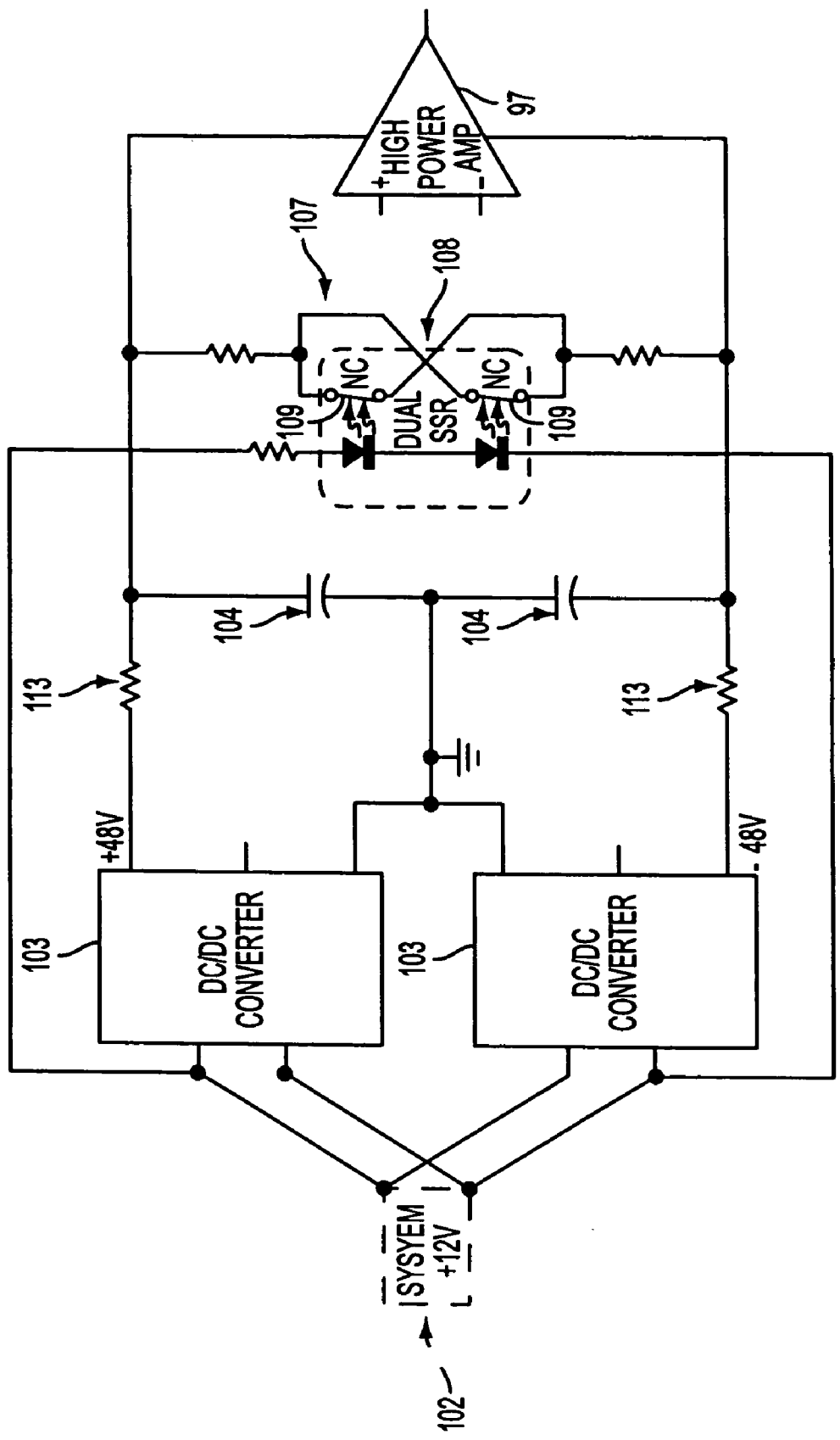
FIG. 19 depicts a discharge circuit for energy storage capacitors that supply electrical pulses to the high power amplifier.
Figure 20:
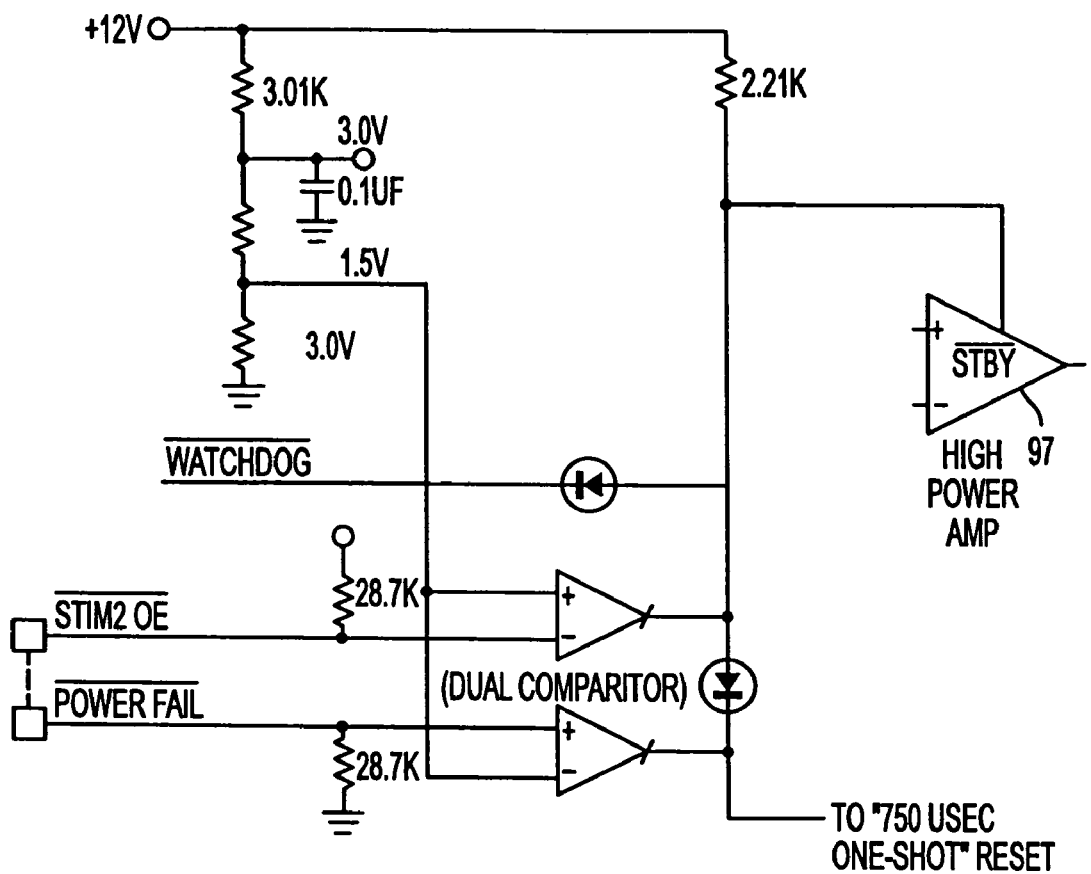
FIG. 20 depicts a standby control circuit for the high power amplifier.

For safety purposes, a discharge circuit 107 shown in FIGS. 18 and 19 is employed to discharge the energy storage capacitors 104 rapidly when the system power supply 102 is lost. As shown in FIG. 19, both poles of a dual normally closed contact solid state relay 108 are connected in parallel from the high voltage side of the positive voltage capacitor 104 to the high voltage side of the negative voltage capacitor 104. The relay 108 is energized by the system power supply 102, causing the relay elements 109 to open to charge the capacitors 104. When the system power supply 102 is lost, however, the relay elements 109 short and the capacitors 104 are discharged. Output of spurious Stim 2 pulses while the system power supply 102 is powering up or down is suppressed via a standby control circuit as represented by FIG.

20, wherein a high signal on Stim 2 OE (output enable) disables the high power amplifier 97. This corresponds to a power-up reset state of the digital channels of the A/D board before the system software takes control. Control for power down (POWER FAIL) comes from a power fail sensor chip on the main amplifier of the main board.

Figure 21:
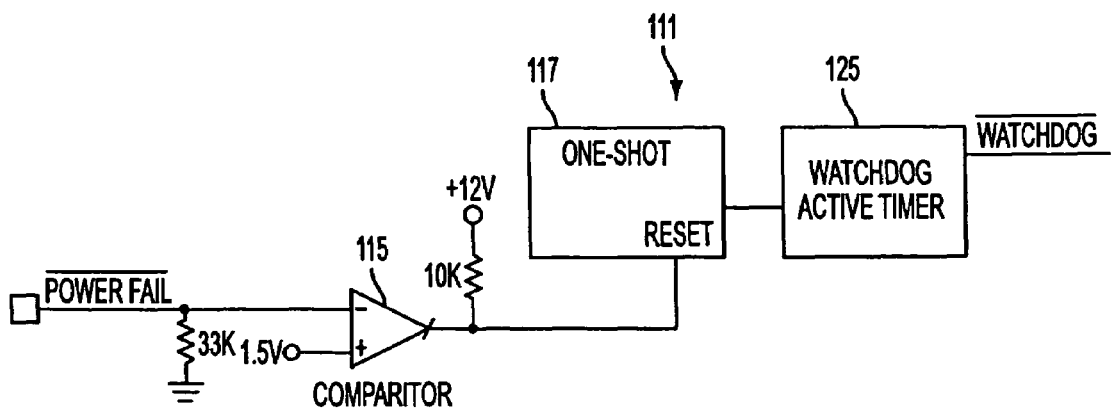
FIG. 21 depicts a watchdog circuit for the high power amplifier.

A watchdog 111, best depicted in FIGS. 18 and 21, protects against excessive Stim 2 electrical stimulation being delivered to the patient in the event of circuit or software malfunction. Limiting resistors 113 in the charge paths for the energy storage capacitors 104 that provide DC power to the high power amplifier 97 also provide protection against overstimulation as shown in FIGS. 18 and 19. The watchdog 111 monitors the duration of Stim 2 pulses, and the presence of a positive or negative pulse greater than a predetermined amplitude of current is detected by a comparator 115 from a current sense resistor as seen in FIG. 21. As shown in FIGS. 18 and 21, a 750 microsecond one-shot 117 is constantly retriggered by a free running clock 119, with retriggering being blocked when a Stim 2 pulse is active. If a Stim 2 pulse is active for more than 750 microseconds, the one-shot 117 will activate a 20 second watchdog active timer 125. The watchdog active timer 125 functions as a self-resetting register which, while activated, causes disablement of the high power amplifier 97, illumination of a watchdog LED, and setting the watchdog status line to the CPU as "true" (high). At the expiration of 20 seconds, the watchdog active timer 125 resets, thereby canceling the watchdog condition. The high power amplifier 97 is reenabled, the LED turns off, and the watchdog status line is set to "false" (low). If the conditions that caused the watchdog 111 to become activated persist, the foregoing cycle will repeat with a 750 microsecond Stim 2 pulse occurring every 20 seconds. The watchdog 111 will be triggered by a power fail detection, generating at least 20 seconds of Stim 2 inactivation in the event of a momentary power interruption. Triggering of the watchdog 111 causes an immediate reset of the watchdog active timer 125.

Figure 22:
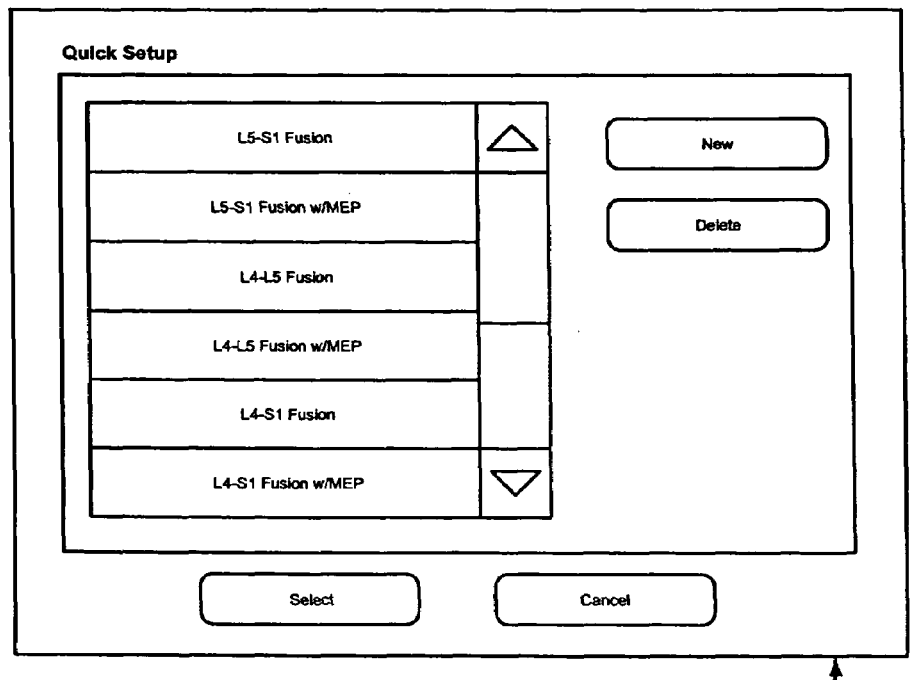
FIG. 22 illustrates a quick setup display for a touch screen of the power console.

The user interface 21 presents various displays on the touch screen 30 providing information and providing control options for executing various selections, features or functions. Control options may comprise various touch-on or press-on graphics including but not limited to check boxes, radio buttons, adjustment buttons and arrows, scroll buttons and arrows, word commands, information boxes, and LED indicators. Upon start-up, the touch screen normally defaults to a quick setup display 127 as represented in FIG. 22. The quick setup display 127 lists various predefined setups for various surgical procedures as well as custom setups previously entered by a user into the software of the monitoring system 10. Setups designated "w/MEP" include muscles that are to be monitored for motor evoked responses. Representative but not limiting surgical procedures for which predefined setups may be listed on the quick setup display 127 include fusions at spinal levels L5-S1, L4-L5, L4-S1, L3-L4 and L2-L3, with and without MEP. Scroll buttons including up and down arrows allow the list of setups to be scrolled up and down. Pressing a desired setup highlights the setup, and thereafter pressing a "select" button opens an EMG or Stim 1 monitoring display with values for the selected setup loaded and displayed. Pressing "new" closes the quick setup display 127 and opens a nerve root selection display to begin a custom setup. Pressing "cancel" loads factory default settings, closes the quick setup display 127 and opens the EMG monitoring display with the default settings loaded. Pressing "delete" opens a delete confirmation display allowing a custom setup to be deleted.

Figure 23:
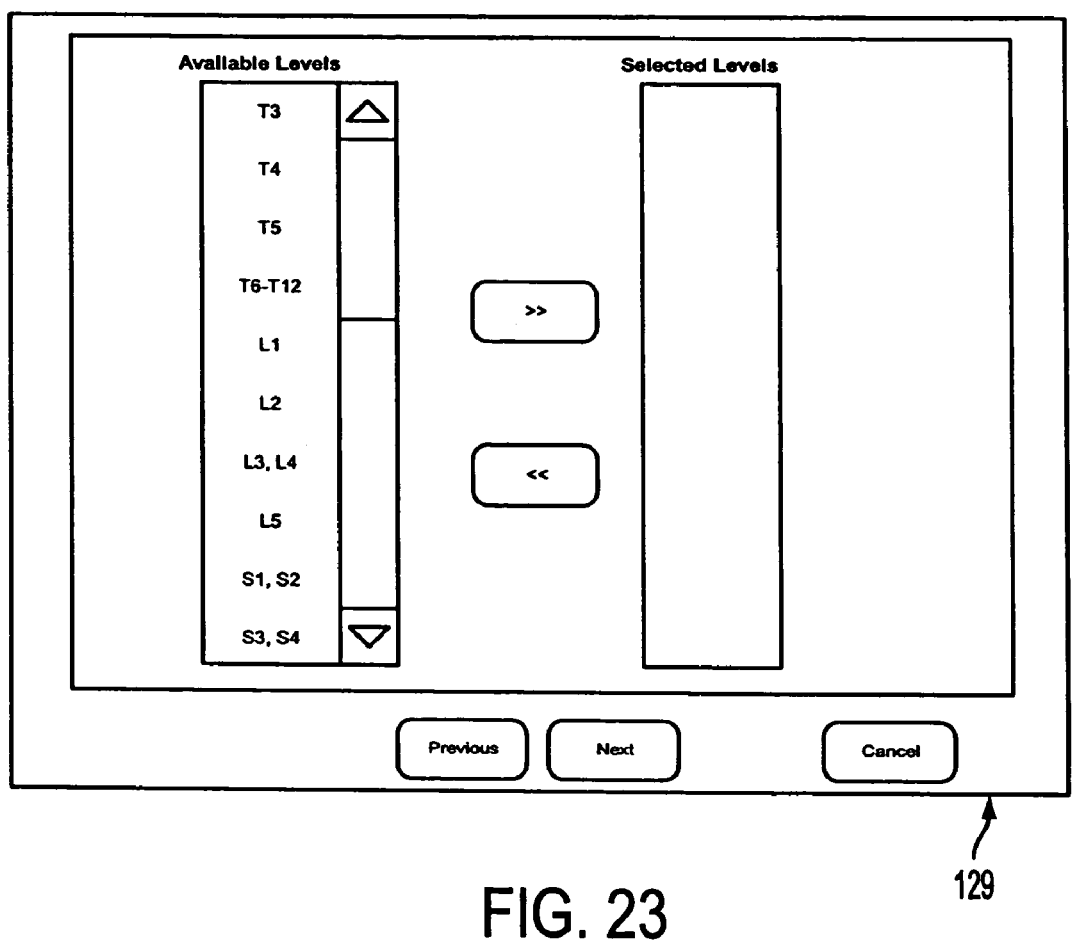
FIG. 23 illustrates a nerve root selection display for the touch screen.

The nerve root selection display 129 is illustrated in FIG. 23. A window of the nerve root selection display 129 lists "available levels" of nerve roots, e.g. C3-C7, T1-T12, L1-L5, S1 and S2, which may be selectively moved to and from a "selected levels" window via right and left directional arrow buttons. The nerve root levels listed in the "available levels" window may be scrolled up and down by pressing scroll buttons including up and down arrows. Pressing a "previous" button closes the nerve root selection display 129 and reopens the quick setup display 127. Pressing a "cancel" button loads factory default settings, closes the nerve root selection display 129 and opens the EMG monitoring display with the default settings loaded. A "next" button may be pressed in order to open a montage display presenting the recommended muscle montage for the selected nerve root levels.

Figure 24:
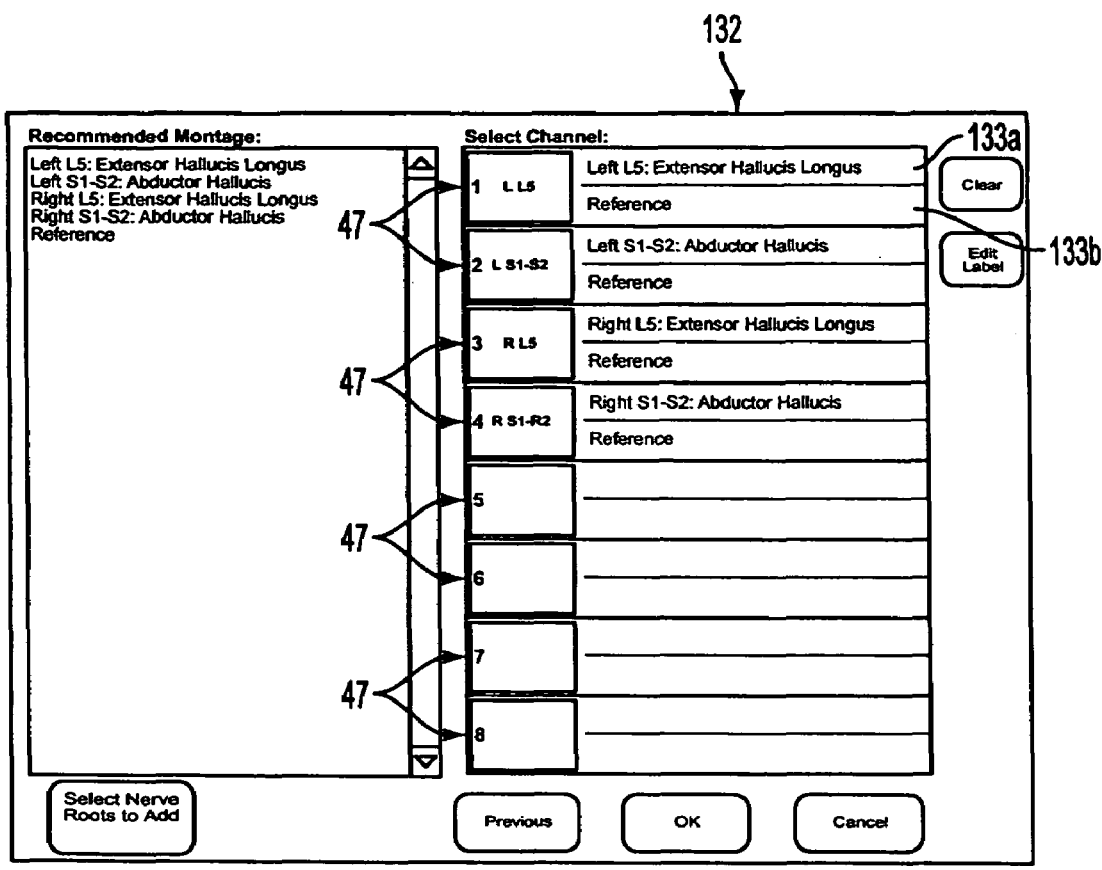
FIG. 24 illustrates a montage display for the touch screen.

FIG. 24 illustrates a representative montage display 132. The montage display 132 includes a "recommended montage" window presenting a list including "reference" as well as the particular muscles recommended for monitoring based on the surgical procedure and/or nerve root levels previously selected via the quick setup display 127 or the nerve root selection display 129. Each muscle listed includes the muscle name, location (right or left side of the patient's body) and nerve root level(s). The list can be scrolled up and down using scroll buttons comprising up and down arrows. A "select channel" window of the montage display 132 has channel divisions corresponding to the monitoring channels 47, respectively. Each channel division includes a channel label, having the number of the channel thereon, and electrode assignment boxes 133a and 133b respectively corresponding to the positive and negative monitoring electrode inputs for the channel. The two monitoring electrodes 50a, 50b for a channel 47 may be connected from one muscle to another (muscle-to-muscle montage), thereby expanding monitoring capability, from a muscle to an electrically neutral reference such as the skin (muscle-to-reference montage), or together in the same muscle (intra-muscle montage). The montage display 132 shown by way of example in FIG. 24 is representative of a muscle-to-reference montage.

For a muscle-to-muscle montage, a muscle listed in the "recommended montage" window, e.g. Left L5: Extensor Hallucis Longus, may be selected by pressing on the muscle listing and may be assigned to a channel 47, e.g. channel 1, by pressing the electrode assignment box 133a for the positive monitoring electrode input for the channel. The muscle listing will remain in the "recommended montage" window but will also appear in the electrode assignment box 133a of the channel. The corresponding channel label will be set to the location, i.e. L (left) or R (right), and the range of nerve root levels for the muscle, e.g. L5. Another muscle listed in the "recommended montage" window may be selected and assigned in a similar manner to the electrode assignment box 133b for the negative monitoring electrode input of the same channel to complete the montage. The channel label will remain the same, and the listing for the second muscle will appear in the electrode assignment box 133b for the channel. The muscle-to-reference montage is similar to the muscle-to-muscle montage except that "reference" is selected in the "recommended montage" window instead of the second muscle and is assigned to the electrode assignment box 133b for the negative monitoring electrode of the channel. To establish an intra-muscle montage, the same muscle selected and assigned to the electrode assignment box 133a for the positive monitoring electrode input of the channel is selected and assigned to the electrode assignment box 133b for the negative monitoring electrode input of the channel. For each type of montage, the channel label continues to display the location ("R" or "L") and the range of nerve root levels for the muscle assigned to the positive monitoring electrode input.

Channel assignments may be cleared using a "clear" button on the montage display 132. A channel label may be customized for other nerve roots by pressing an "edit label" button which provides access to a keyboard display for the entry of alphanumeric characters. A "cancel" button may be used to load factory default settings, close the montage display 132 and open the EMG monitoring display. Pressing a "previous" button saves the channel assignments and opens the nerve root selection display 129. An "OK" button is pressed in order to save the channel assignments, close the montage display 132 and open the EMG monitoring display. A "select nerve roots to add" button may be used to save channel assignments and open a display by which additional nerve roots may be entered and added to the montage display 132.

Figure 25:
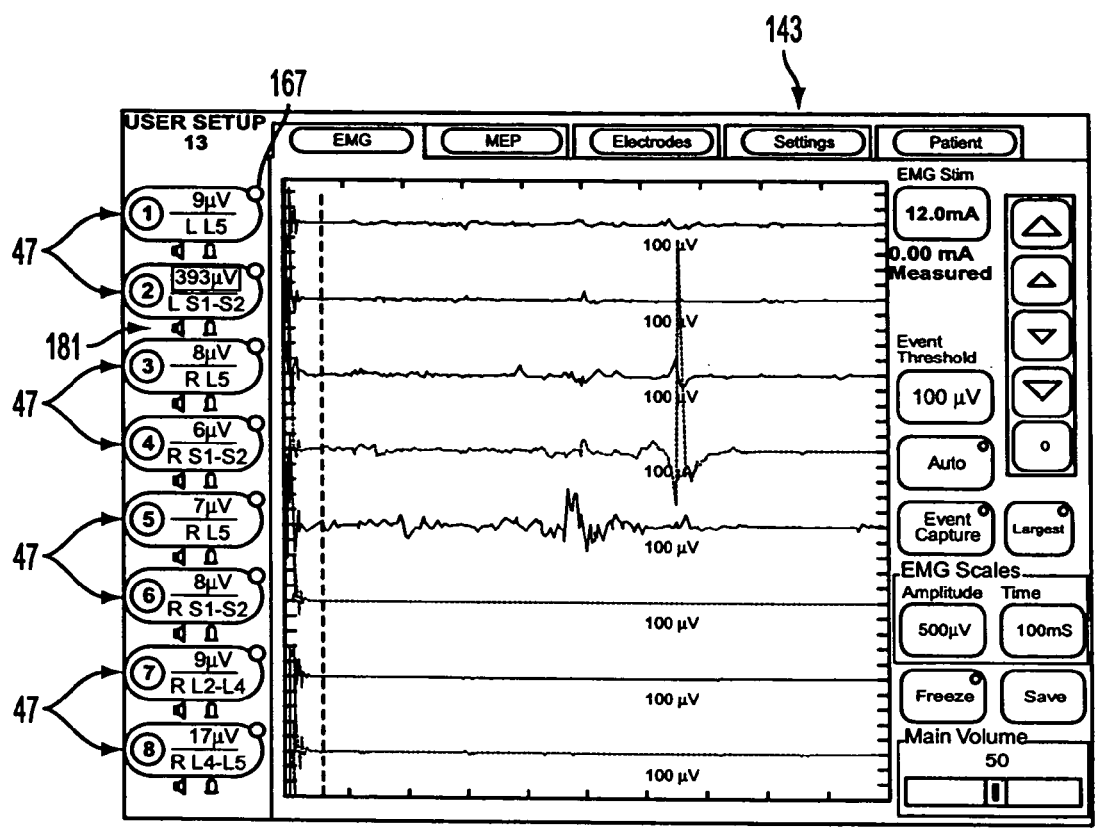
FIG. 25 illustrates a monitoring display for the touch screen for Stim 1 electrical stimulation.

The EMG monitoring display 143 is illustrated in FIG. 25 and is used for continuous EMG monitoring and for EMG monitoring when Stim 1 electrical stimulation is applied to the patient. The EMG monitoring display 143 includes a channel button and a waveform display area for displaying waveforms representative of EMG activity detected by the monitoring electrodes 50a, 50 for each monitoring channel 47 in use. The waveform display area has a vertical scale (amplitude) and a horizontal scale (time). The vertical scale is divided into forty divisions with each channel 47 allocated a segment of five divisions (2½ positive, 2½ negative) to accommodate the biphasic EMG waveforms. Each segment represents a reference value for the vertical scale of 50, 200, 500 or 2000 microvolts as selected by pressing an "amplitude" button on the display. Where 500 microvolts is selected for the reference value of the vertical scale as shown in FIG. 25, for example, the value for each division of the vertical scale is 100 microvolts. The horizontal scale is divided into ten divisions. Reference values of 50 milliseconds, 100 milliseconds or 10 seconds may be selected for the entire horizontal scale by pressing a "time" button on the EMG monitoring display 143. Where 100 milliseconds is selected as the reference value for the horizontal scale as illustrated in FIG. 25, for example, each division of the horizontal scale equals 10 milliseconds. It should be appreciated that other reference values for the vertical and/or horizontal scales of the EMG monitoring display 143 may be made available for selection by the user. Changing the reference values for the vertical and horizontal scales affects how the waveform data appears on the display 143 without modifying the monitoring sensitivity. At start-up, a sample of baseline EMG activity is displayed for each monitoring channel 47 in use. Typically, when the nerve being monitored is not being manipulated or electrically stimulated, little or no EMG activity is detected. The amplitude of ongoing baseline signals will typically be small, usually 10–30 microvolts.

The channels 47 may be turned on and off by pressing the channel buttons on the EMG monitoring display 143, which also activates and deactivates LED indicators 167 on the channel buttons. Each channel button is identified by the channel number, and the channel button of each channel 47 being used for monitoring displays the location ("L" or "R") and nerve root level(s) being monitored. During power-up, each channel 47 that is coupled with a patient connected monitoring electrode is automatically turned on. Tone and audio icons 181 for the channel buttons are enabled when a channel mute function is selected via a settings display accessed by pressing a "settings" tab on the EMG monitoring display 143. The icons indicate, respectively, whether event tones and EMG audio are turned on or off.

The EMG monitoring display 143 has an "EMG Stim" box depicting the stimulation level (current amplitude) selected for Stim 1 electrical stimulation. The level is selected by pressing the "EMG Stim" box and then pressing the appropriate up or down coarse or fine adjustment arrow buttons to obtain a level from 0 to 30 mA. The "EMG Stim" box and the adjustment arrow buttons associated therewith provide a stimulation level selector or control option for the Stim 1 electrical stimulation delivered by the stimulating probe. The current level will typically be set to zero when Stim 1 electrical stimulation is not in use. When Stim 1 electrical stimulation is delivered to the patient using a monopolar or bipolar stimulating probe as described above, the "measured" current amperage delivered to the patient is displayed adjacent the "EMG Stim" box. Pressing the "0" button will reset the stimulus level to zero.

An "event threshold" button of the EMG monitoring display 143 is used to adjust an event threshold of the monitoring system 10. The event threshold is enabled by an event threshold filter and assists in defining where monitored EMG activity becomes significant. EMG activity that exceeds the event threshold is considered an "event", resulting in an audible event tone. The event threshold is adjusted by pressing the "event threshold" button and then pressing the appropriate up or down coarse or fine adjustment arrow buttons associated with the "event threshold" button. The "event threshold" button and associated adjustment arrow buttons provide a control option for the user to select or adjust the event threshold. The total adjustable range for the event threshold is preferably 20–2500 microvolts. The level of EMG activity selected as the event threshold, e.g. 100 microvolts as shown by way of example in FIG. 25, will be indicated on the EMG monitoring display 143. The "auto" button may be used as a control option to automatically adjust the event threshold to maximize EMG information. Where EMG activity has exceeded the event threshold for 10–20 seconds, for example, the event tones lose their usefulness and simply become noise. If "auto" is selected, this 10–20 seconds of EMG activity will be averaged and a new event threshold will be set. All EMG activity smaller than the new event threshold can be heard as raw EMG, while EMG activity greater than the new event threshold will generate event tones, thereby maximizing information and minimizing unnecessary noise.

An "event capture" button on the EMG monitoring display 143 allows EMG waveforms that exceed the event threshold, i.e. events, to be captured in the waveform display area of the EMG monitoring display. The event capture function is turned on and off by pressing the "event capture" button. When the event capture function is turned on, waveforms that exceed the event threshold are captured on the display and remain captured on the display until replaced by the next captured event. In addition, any channel having EMG activity resulting in a captured event will have the amplitude of the last captured event displayed on its channel button. Having the event capture function turned on also allows a particular event waveform on the display 143 to be pressed, causing the amplitude and time for the event waveform to be displayed. When the event capture function is turned off, the channel buttons display the amplitude of monitored EMG activity. While the event capture function is used to capture current events, a "largest" button may be turned on to effect capture of the largest in a series of events.

The "largest" button is turned on and off by pressing and is used with the 50 millisecond or 100 millisecond time scale. For example, if fifteen sequential events occurred and the fourth event was the largest, a trace of the fourth event would be displayed along with "4 of 15".

The EMG monitoring display 143 is identified by a highlighted "EMG" tab and presents additional tabs for "MEP", "electrodes", "settings" and "patient" displays accessible by pressing the corresponding tabs. The EMG monitoring display 143 may have a "freeze" button for freezing a current display, a "print" button for transmitting a current display as image or text to a printer, a "save" button for sending a current display to a compact flash disk, a "?" button (not shown) for opening a "help" screen for a current display, and/or a "volume" control button for adjusting speaker/headphone volume.

Figure 26:
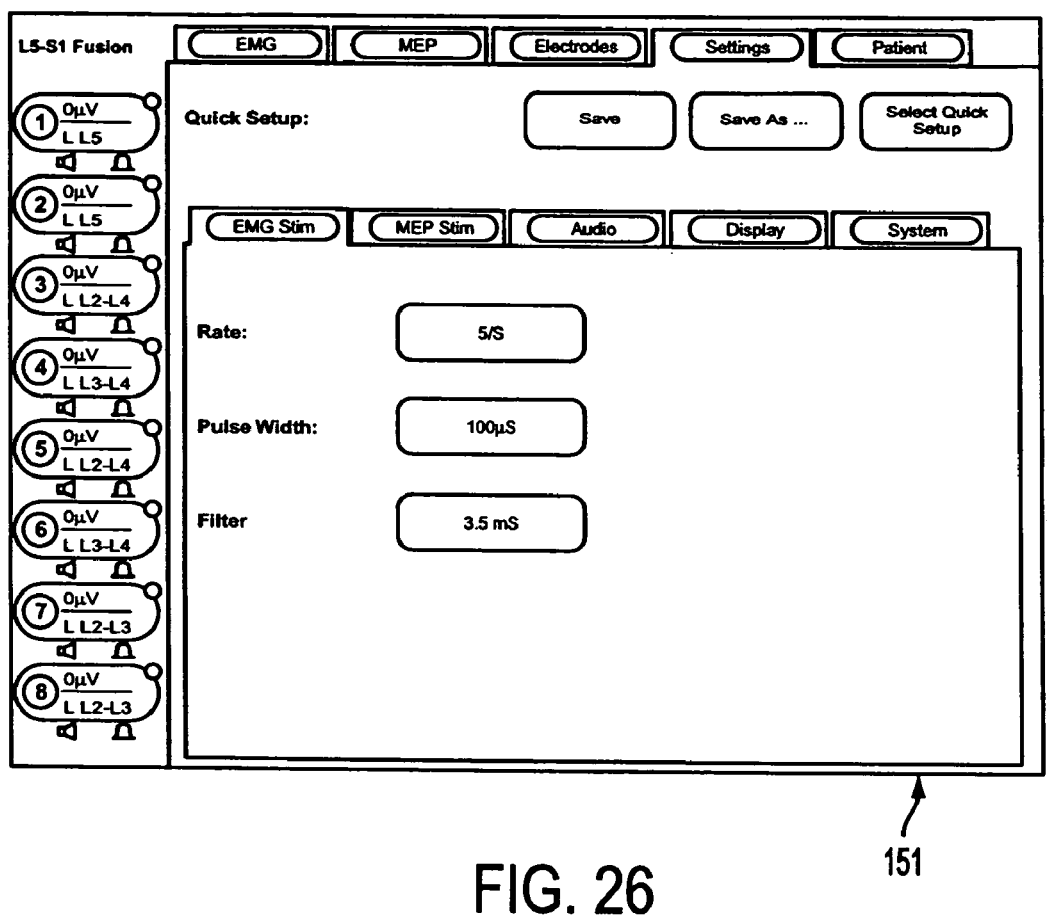
FIG. 26 illustrates a settings display for the touch screen by which parameters are selected for Stim 1 electrical stimulation.

Rate, pulse width and artifact delay for Stim 1 electrical stimulation are selected using an EMG Stim settings display, an example of which is depicted at 151 in FIG. 26. The EMG Stim settings display 151 is accessed by pressing the "settings" tab on the EMG monitoring display 143. Rate is selected by pressing a rate box on the settings display 151 to toggle through the preset values of 1, 5 or 10 pulses/second. Pulse width is selected by pressing a pulse width box on the settings display 151 to toggle through the preset values of 50, 100, 150, 200 and 250 microseconds. Artifact is the electronic noise that exists after a stimulus pulse is applied, and artifact delay is a selectable period of time after stimulation during which EMG activity is ignored so that the actual stimulus response is distinguished from the effects of artifact. As seen in FIG. 25, a vertical dashed line in the waveform display area of the EMG monitoring display 143 during stimulation separates the artifact delay from the beginning of true EMG activity. The artifact delay is effected via a software filter, and the duration of the artifact delay, i.e. the delay between the end of the last stimulating pulse and the beginning of true EMG data, is selectable by pressing a filter box on the settings display 151. Pressing the filter box causes coarse and fine adjustment arrow buttons to appear for incrementally adjusting the artifact delay within a range of about 1.0 to 8.0 milliseconds.

Figure 27:
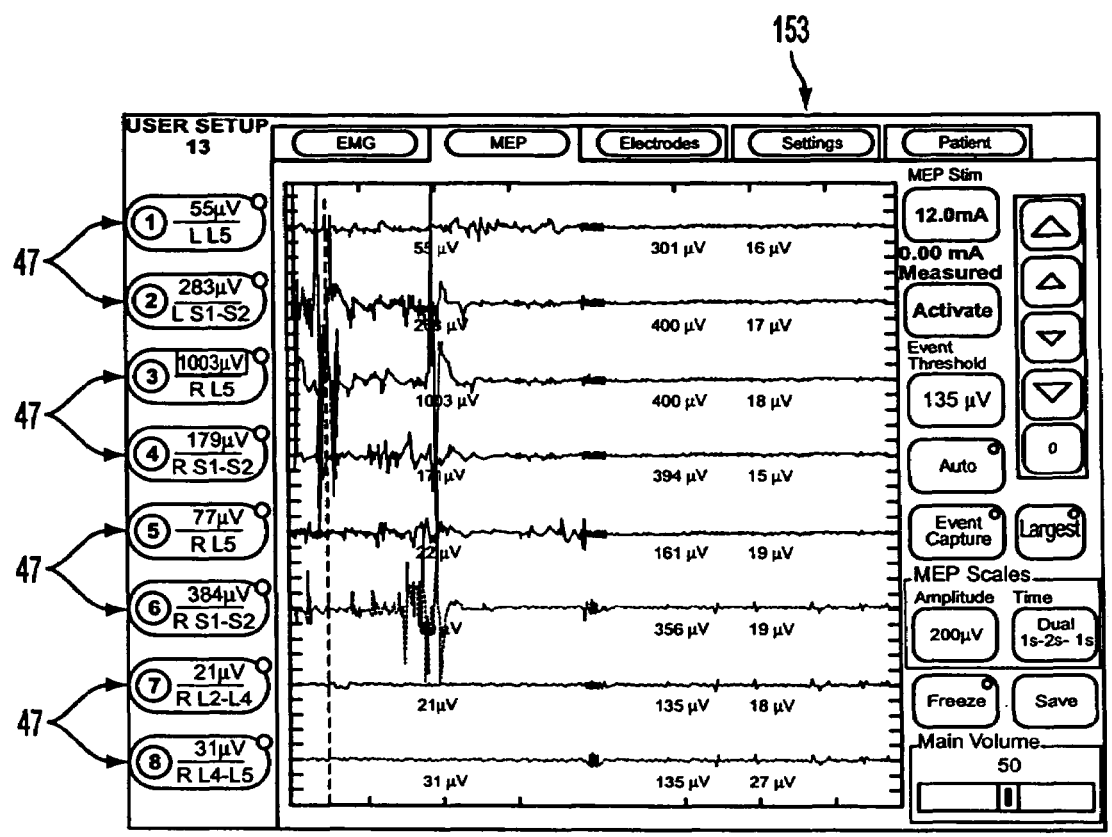
FIG. 27 illustrates a monitoring display for the touch screen for Stim 2 electrical stimulation.

An MEP or Stim 2 monitoring display 153 is shown in FIG. 27 and is accessed by pressing the "MEP" tab on the EMG monitoring display 143. The MEP monitoring display 153 is used when Stim 2 electrical stimulation is to be applied to the patient and comprises channel buttons, a waveform display area for displaying EMG activity detected by the monitoring electrodes for each monitoring channel in use, buttons for "event threshold", "auto", "event capture", "largest", "0", "amplitude", "time", "freeze" and "save", a volume control, and tabs for accessing additional displays as described above for the EMG monitoring display 143. The MEP monitoring display 153 may also include a "?" button for accessing a help display. The MEP monitoring display 153 includes a stimulation level selected for the stimulator 16 comprising an "MEP Stim" button and coarse and fine adjustment arrow buttons associated with the "MEP Stim" button. The "MEP Stim" button displays the selected level (current amplitude) for Stim 2 electrical stimulation, which is selected or adjusted by the user via the coarse and fine adjustment arrow buttons on the display 153, which further includes an indicator showing "measured" amperage for delivered Stim 2 current. The level for Stim 2 electrical stimulation is adjustable from 0 to 200 mA. If the selected stimulation level exceeds 30 mA, a dialog box will open requiring the selected level to be accepted or canceled. Pressing "0" resets the stimulation level to zero. An "activate" button of the MEP monitoring display 153 is pressed as the first step in a multi-step manual actuation procedure required to start delivery of Stim 2 electrical stimulation from the stimulator 16. Pressing the "activate" button opens a dialog box requiring the activation to be accepted or canceled as a second step in the manual actuation procedure. If accepted, a complete cycle of Stim 2 electrical stimulation will be delivered from the stimulator 16. Accordingly, actuation via the touch screen 30 is implemented using an activator or control options of the touch screen, i.e. the "activate" button and the acceptance dialog box, and the activator is operable or actuatable by a user completing performance of a two-step manual actuation procedure with the activator to start delivery of the Stim 2 electrical stimulation. Requiring completion of a multi-step manual actuation procedure to start delivery of Stim 2 electrical stimulation avoids erroneous or inadvertent actuations. Actuation of the activator to complete the actuation that starts delivery of Stim 2 electrical stimulation from stimulator 16 is effective to deliver a complete cycle of selected monophasic or biphasic Stim 2 stimulation from stimulator 16.

The vertical scale of the waveform display area of the MEP monitoring display 153 is the same as the vertical scale of the EMG monitoring display 143 and the reference value for each segment of the display area is selectable as described for the EMG monitoring display 143. The horizontal scale for the waveform display area of the MEP monitoring display 153 has three sections, i.e. left, middle and right, and the MEP monitoring display requires that the "time" button be set at "dual 0.1 s-2 s-0.1 s". The left section represents 0.1 seconds (100 milliseconds), the middle section is compressed and represents two seconds, and the right section represents 0.1 seconds (100 milliseconds). In monophasic Stim 2 stimulation, all of the pulses in a stimulation cycle and the artifact delay following the last pulse in the cycle are applied within the left section of the display area within the first 12 milliseconds. The next 88 milliseconds of the left section is where EMG events would appear should they occur, and a vertical dashed line in the left section of the waveform display area during stimulation distinguishes the artifact delay from the beginning of actual EMG activity. Following the two second delay in the compressed middle section, monitored EMG activity continues in the right section of the waveform display area during the next 100 milliseconds. In biphasic Stim 2 stimulation, the first group of pulses in a stimulation cycle and the artifact delay following the last pulse of the first group are applied within the left section of the waveform display area as described for monophasic Stim 2 stimulation. The middle section is a compressed time delay allowing the muscles to relax before the second group of pulses in the stimulation cycle is applied. The second group of pulses and the artifact delay following the last pulse of the second group are applied within the right section of the waveform display area within the first 12 milliseconds of the right section. The next 88 seconds of the right section reflects monitored EMG activity where EMG events would appear should they occur.

Figure 28:
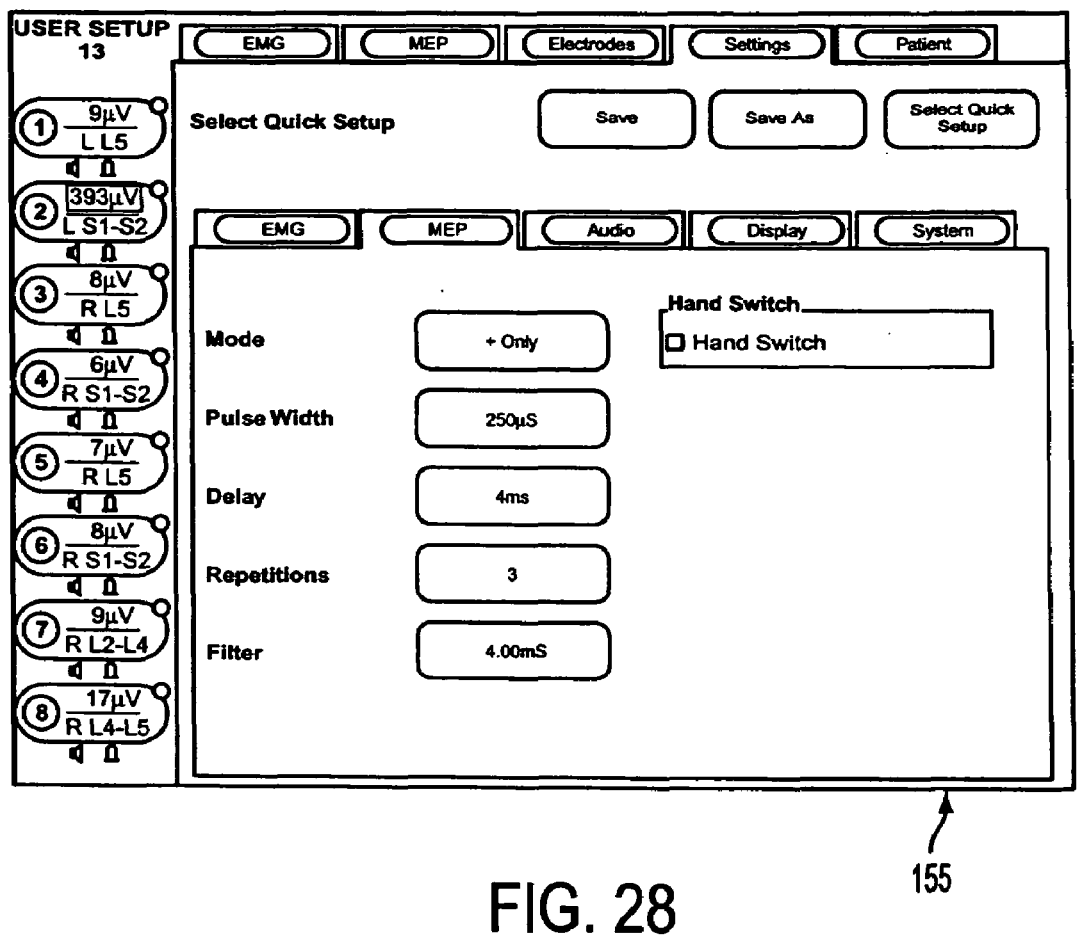
FIG. 28 illustrates a settings display for the touch screen by which parameters are selected for Stim 2 electrical stimulation.

An MEP Stim settings display 155 shown in FIG. 28 is accessed via the "MEP Stim" tab on the EMG settings display 151 and has control options for the user to select mode, pulse width, delay, repetitions and artifact delay for Stim 2 electrical stimulation. The MEP Stim settings display 155 is similar to the EMG settings display 151 but has a mode selector for stimulator 16 including a box or control option for selecting the mode of Stim 2 electrical stimulation to be delivered by stimulator 16 upon completion of the multi-step actuation procedure. The mode selector has settings selectable by a user prior to actuation of the activator for stimulator 16. The mode selector has a negative monophasic mode setting ("– only") by which the stimulator 16 is pre-set to deliver a complete cycle of monophasic Stim 2 electrical stimulation in a negative monophasic mode (all pulses negative; the mode selector has a positive monophasic mode setting ("+ only") by which the stimulator 16 is pre-set to alternatively deliver a complete cycle of monophasic Stim 2 electrical stimulation in a positive monophasic mode (all pulses positive; the mode selector has a negative leading biphasic mode setting ("–=+") by which the stimulator 16 is pre-set to alternatively deliver a complete cycle of biphasic Stim 2 electrical stimulation in a negative leading biphasic mode (negative pulses followed by positive pulses; and the mode selector has a positive leading biphasic mode setting ("+=–") by which the stimulator 16 is pre-set to alternatively deliver a complete cycle of biphasic Stim 2 electrical stimulation in a positive leading biphasic mode (positive pulses followed by negative pulses). The MEP Stim settings display 155 also has a pulse width selector or control option operable by the user to set the pulse width, i.e. 100, 250 or 500 microseconds, for the pulses of Stim 2 electrical stimulation, a delay selector or control option operable by the user to set the delay, i.e. 2, 3 or 4 milliseconds, between pulses of Stim 2 electrical stimulation, a repetition selector or control option operable by the user to select pulse repetitions, i.e. a group of 1–8 positive or negative pulses in a monophasic cycle of Stim 2 electrical stimulation or a first group of 1–8 positive or negative pulses followed by a second group of the same number of pulses of reverse polarity in a biphasic cycle of Stim 2 electrical stimulation, and an activator selector or control option operable by the user to select hand switch actuation. The MEP Stim settings display 155 also has a filter button for adjusting the artifact delay as described above for the EMG Stim settings display 151, although the artifact delay for MEP Stim (Stim 2) will typically be adjustable within a range of 1.0 to 16.0 milliseconds.

Figure 29:
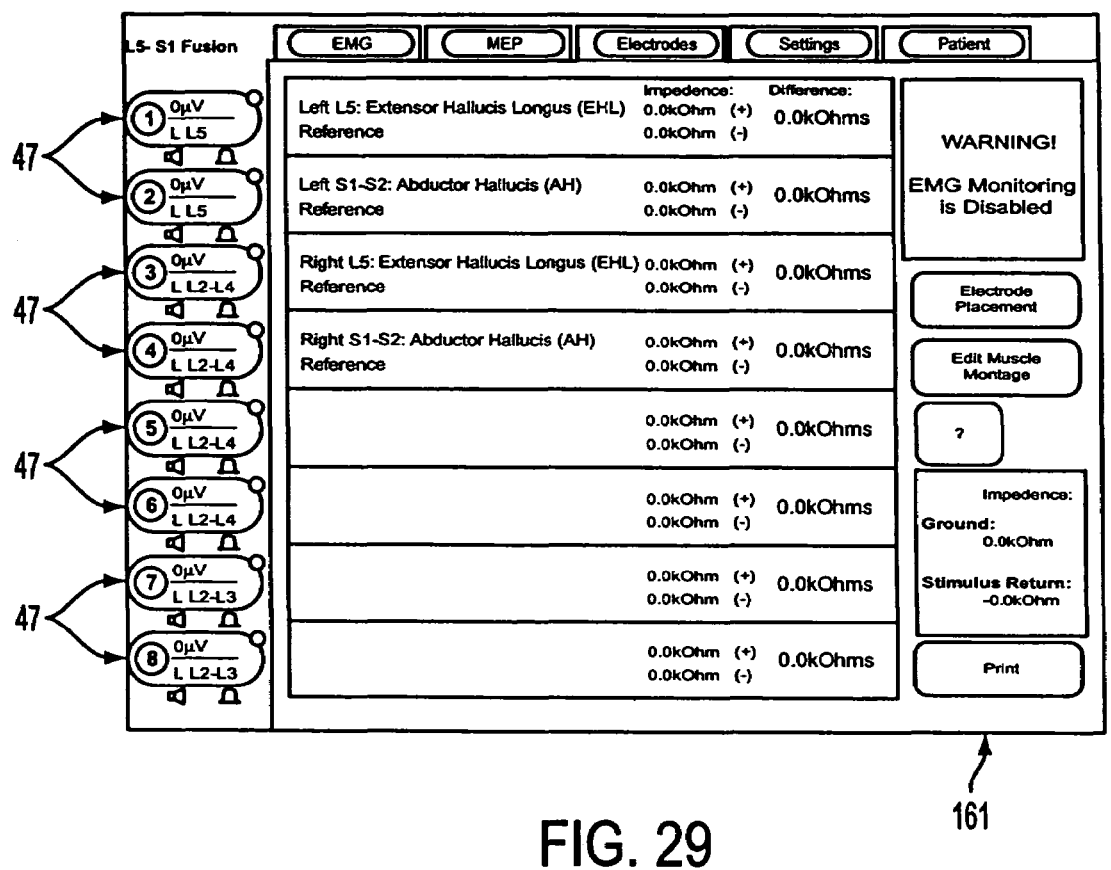
FIG. 29 illustrates an electrodes display for the touch screen.

FIG. 29 illustrates an electrodes display 161 that may be accessed via the "electrodes" tabs on the EMG and MEP monitoring displays to confirm proper placement of the monitoring electrodes prior to intraoperative monitoring. The electrodes display 161 displays the positive and negative impedance of connected monitoring electrodes 50a, 50b for each monitoring channel 47, the calculated difference in their values, the impedance of the ground electrode 54, the impedance of the return electrode (anode) 60, and electrode to muscle placement. The difference in impedance for the electrodes 50a, 50b of each monitoring channel 47 must be within an acceptable range and, if a difference falls outside of the accepted range, it is indicated on the electrodes display 161 by a red box and reversed text or may be differentiated in any other suitable manner allowing the cause of the problem to be identified and resolved. Actions which may be taken to resolve an impedance difference that is outside the accepted range include reinserting the electrode(s) in question, replacing the electrode(s) in question with a new electrode(s) and/or checking the connection for the electrode(s) in question with the patient interface unit. A ground electrode and/or return electrode having an impedance greater than 10 kOhms must be replaced with an electrode resulting in an impedance of 10 kOhms or less. The inserted location of each monitoring electrode is described next to the corresponding channel button. The electrodes display 161 can be printed or saved to a compact flash disk using a "print" button or other appropriate button provided on the electrodes display. EMG monitoring via the monitoring electrodes is disabled whenever the electrodes display 161 is opened. The montage display 132 may be accessed from the electrodes display 161 via an "edit muscle montage" button of the electrodes display 161 in order to add and/or change electrode information. An electrode placement display may be accessed from the electrodes display 161 via an "electrode placement" button of the electrodes display 161 and may comprise various sub-displays graphically or pictorially presenting the suggested anatomical placement for the monitoring electrodes for the monitoring of various nerves/nerve root levels for the factory preset spinal levels or divisions.

A patient display is accessible via the "patient" tabs on the EMG and MEP monitoring displays for the entry of patient information including patient name and identification number, procedure and comments. Information may be entered using a keyboard which opens on the touch screen 30 as the user interacts with the patient display.

The intraoperative neural monitoring system 10 produces various sounds including EMG audio, event tones, baseline voices, stimulation tones and voices, and help voices which are selectable and/or adjustable using an audio settings display (not shown) accessed via an "audio" tab of the EMG Stim and MEP Stim settings displays 151,155. EMG audio is the amplified sound of muscle activity detected by the monitoring electrodes and may be heard as a low-pitched drumbeat, a high-pitched crackle or a growl. Other EMG audio responses include brief burst responses caused by electrical stimulation, direct nerve contact, irrigation or thermal changes, longer train responses caused by nerve excitation or irritation, irrigation, drying, bumping or anesthesia, and repetitive pulse responses caused by electrical stimulation, tumor mapping or verification of nerve integrity.

EMG audio may be selected/deselected using a button on the audio settings display. All EMG activity is audible when EMG audio is turned on. Event tones are heard when the monitored EMG amplitude is greater than the event threshold setting. The event tones are different for each monitoring channel, increasing in pitch from channel one to channel eight so that the channels responsible for the event tones may be identified. Event tones are also selected/deselected using a button on the audio settings display. A channel may be configured to produce both EMG audio and event tones, EMG audio alone or event tones alone as enabled via a channel mute button on the audio settings display and as indicated by the icons 181 shown in FIG. 25.

Stimulation tones and voices exist in opposite states, i.e. if one is selected the other is disabled. These selections are made using appropriate buttons on the audio settings display. Stimulation voices announce the delivery of stimulus current to the surgical field by voice. Delivery of Stim 1 stimulus may be announced by the word "stimulus" along with the preselected current level. Adjustments in the stimulus current may also be announced by voice. Stimulation tones may announce the delivery of Stim 1 stimulus with a continuous warble tone or a brief three beep tone as selected using buttons on the audio settings display. Delivery of monophasic Stim 2 stimulus may be announced by the word "stimulus". Delivery of biphasic Stim 2 stimulus may be announced by the word "stimulus" followed by a continuous tone which is followed by the word "stimulus". Stimulation tones may announce the delivery of monophasic Stim 2 stimulus with a brief three beep tone and may announce the delivery of biphasic Stim 2 stimulus with a warble, followed by a continuous tone followed by another warble.

Baseline voices may include baseline increased, baseline decreased and baseline normal voices used in conjunction with the auto threshold feature when automatic adjustments are made. Help voices for "check electrode" and "muting" may be turned on and off via the audio settings display and operate in conjunction with a bleedle alarm. The bleedle alarm, followed by the "check electrode" help voice, signifies the need to check an electrode. The bleedle alarm followed by the "muting" help voice operates when not in the check electrode mode to indicate that the system has been in the mute mode for more than thirty seconds. A beep alarm is generated to indicate failure of internal microprocessor hardware. The audio settings display may include a control for adjusting volume higher or lower.

Figure 30:
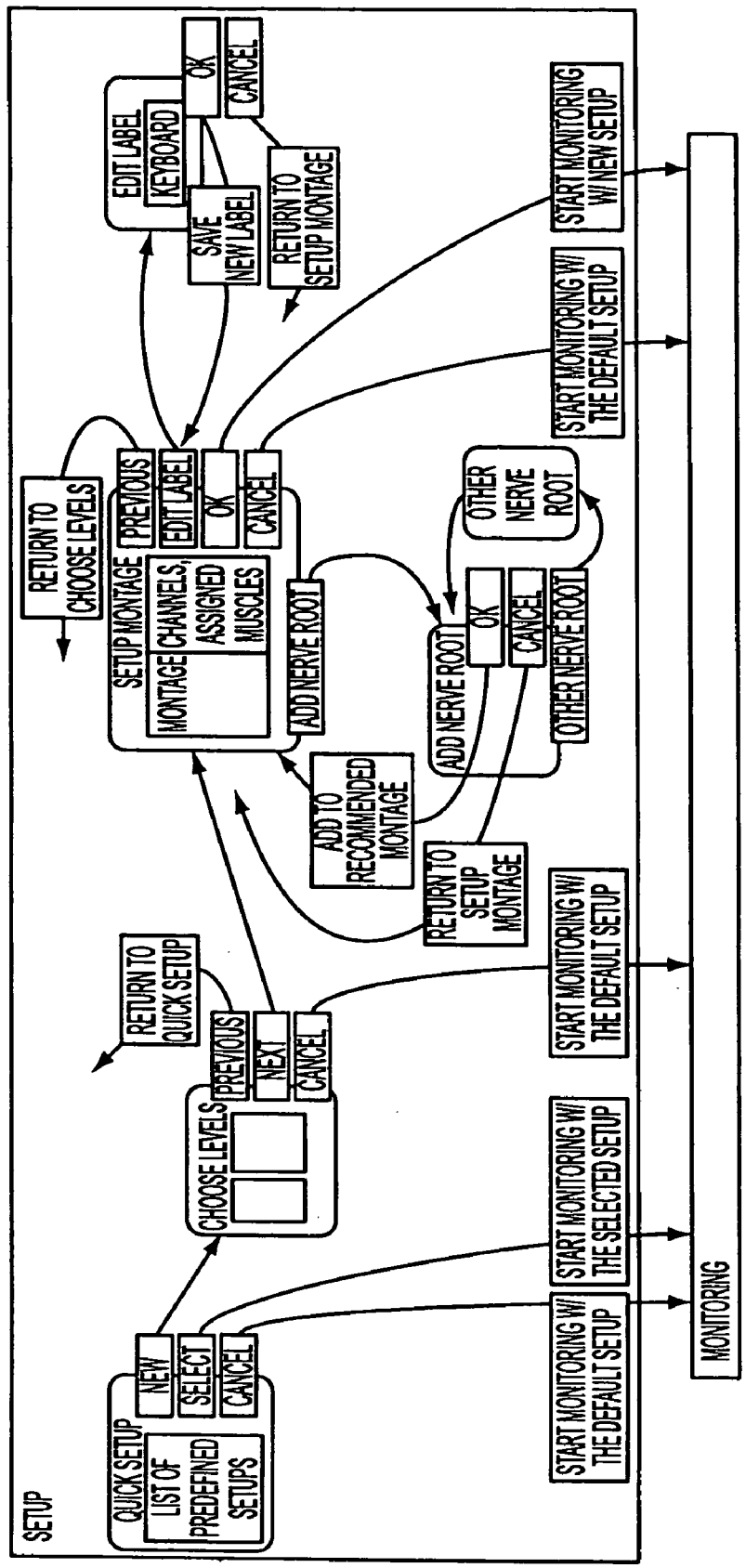
FIG. 30 is a flow diagram depicting the steps that may be undertaken in a set-up mode for the intraoperative neural monitoring system.
Figure 31:
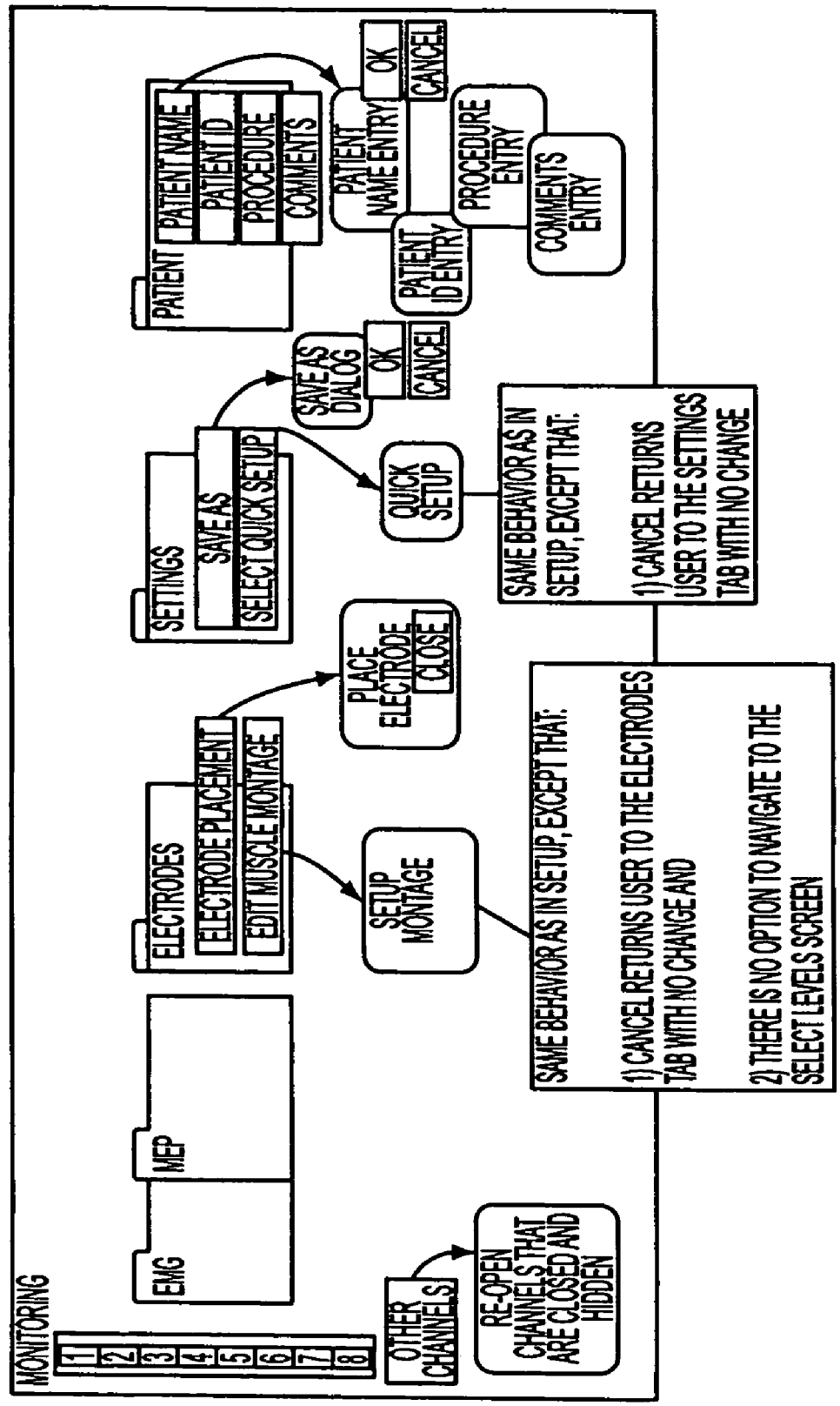
FIG. 31 is a flow diagram depicting the steps that may be undertaken in a monitoring mode for the intraoperative neural monitoring system.

FIG. 30 depicts a flow diagram showing the steps involved when using the intraoperative neural monitoring system 10 during a setup mode, preparatory to a monitoring mode, and FIG. 31 depicts a flow diagram illustrating the steps involved when using the intraoperative neural monitoring system 10 in the monitoring mode.

The intraoperative neural monitoring system is particularly suited for use during surgeries in which a motor nerve is at risk due to unintentional manipulation. It provides patient-connected neural monitoring for various surgical procedures including but not limited to degenerative treatments, scoliosis and deformity cases, pedicle screw procedures, fusion cages, rhizotomy, orthopedic surgery and open and percutaneous lumbar, thoracic and cervical procedures. EMG activity from muscles innervated by nerves is detected via monitoring electrodes placed in the muscles. EMG activity may be monitored continuously and in response to electrical stimulation of anatomical areas from which an electrical impulse may be transmitted to the monitored muscles. Electrical stimulation delivered by the intraoperative neural monitoring system may be Stim 1 electrical stimulation delivered to anatomical tissue via monopolar or bipolar stimulating probes connected to the patient interface unit. The probes may deliver Stim 1 electrical stimulation directly to anatomical tissue by directly contacting the tips of the probes with the tissue or indirectly by contacting the tips of the probe with a conductive medical device, such as a pedicle screw, disposed in contact with the tissue. Electrical stimulation delivered by the intraoperative neural monitoring system may alternatively be Stim 2 electrical stimulation applied via stimulating electrodes located in the anatomical tissue to be stimulated and connected with the stimulator. Stim 2 electrical stimulation may be delivered at significantly higher current than Stim 1 stimulation and is particularly well suited for eliciting MEPs which may produce EMG responses detectable by the monitoring electrodes. Stim 2 electrical stimulation may also be used for pedicle screw stimulation when higher stimulation currents are needed.

The anatomical areas to which electrical stimulation is delivered may vary depending on the surgical procedure being performed, the nerves being monitored, and the type of stimulation desired to be effected. Representative anatomical areas for the application of Stim 2 stimulation include the motor cortex and the spine. The stimulating electrodes for Stim 2 stimulation may be placed at anatomical areas appropriate to stimulate the left and right areas of the motor cortex, with biphasic stimulation allowing the left and right areas of the motor cortex to be stimulated sequentially to excite the muscles on the left and right sides of the patient's body. Biphasic stimulation is accomplished automatically in that a group of positive or negative pulses is automatically followed by a group of pulses of opposite polarity delivered as a complete cycle of stimulation with no action by the user other than the activation required to initiate delivery of the complete cycle of stimulation. By reducing the actions required to be taken by the user, the intraoperative neural monitoring system greatly simplifies intraoperative neural monitoring for greater efficiency and patient safety. The locations for the monitoring electrodes may vary depending on the nerves/nerve roots being monitored, and the user interface may display recommended locations for various preset and custom surgical procedures and/or nerve root levels.

EMG activity detected by the monitoring electrodes is displayed as waveforms during Stim 1 stimulation on an EMG monitoring display and during Stim 2 stimulation on an MEP monitoring display. EMG activity is also displayed on the monitoring displays when no stimulation is being applied. Where the Stim 2 stimulation is biphasic, the MEP monitoring display differentiates the EMG activity corresponding to each group of pulses in the stimulation cycle. In addition, EMG activity from the left and right sides of the patient's body may be displayed simultaneously and correlated in time for a more accurate assessment of neurological responses. Various parameters for Stim 1 and Stim 2 electrical stimulation are adjustable. Various electrical components, circuits and designs may be used in the intraoperative neural monitoring system to effect delivery of Stim 1 and Stim 2 stimulation. Monitoring may be accomplished simultaneously on up to eight monitoring channels.

Inasmuch as the present invention is subject to many variations, modifications and changes in detail, it is intended that all subject matter discussed above and shown in the accompanying drawings be considered illustrative only and not be taken in a limiting sense.

What is claimed is:

1. An intraoperative neural monitoring system comprising
   a power source;
   a stimulator powered by said power source to deliver electrical stimulation for application to anatomical tissue, said stimulator delivering said electrical stimulation alternatively as a complete cycle of monophasic electrical stimulation having a selected number of positive or negative pulses, or a complete cycle of biphasic electrical stimulation having a first group of a selected number of positive or negative pulses automatically followed by a second group of a selected number of pulses of reverse polarity to said pulses of said first group;
   an activator for said stimulator actuatable by a user of said intraoperative neural monitoring system to start delivery of said electrical stimulation; and
   a mode selector for said stimulator having a monophasic mode setting selectable by a user of said intraoperative neural monitoring system, prior to actuation of said activator, to set said stimulator to deliver said complete cycle of monophasic electrical stimulation in response to actuation of said activator to start delivery of said electrical stimulation, and having a biphasic mode setting alternatively selectable by a user of said intraoperative neural monitoring system, prior to actuation of said activator, to set said stimulator to alternatively deliver said complete cycle of biphasic electrical stimulation in response to actuation of said activator to start delivery of said electrical stimulation.

2. The intraoperative neural monitoring system recited in claim 1 wherein said monophasic mode setting includes a positive monophasic mode setting selectable by the user to set said stimulator to deliver said complete cycle of monophasic electrical stimulation as all positive pulses and includes a negative monophasic mode setting alternatively selectable by the user to set said stimulator to alternatively deliver said complete cycle of monophasic electrical stimulation as all negative pulses.

3. The intraoperative neural monitoring system recited in claim 2 wherein said biphasic mode setting includes a positive leading biphasic mode setting selectable by the user to set said stimulator to deliver said first group of pulses as positive pulses and includes a negative leading biphasic mode setting alternatively selectable by the user to set said stimulator to alternatively deliver said first group of pulses as negative pulses.

4. The intraoperative neural monitoring system recited in claim 3 and further including a stimulation level selector for said stimulator operable by a user of said intraoperative neural monitoring system to set a current amplitude for said pulses from 0 to 200 mA.

5. The intraoperative neural monitoring system recited in claim 4 wherein said stimulation level selector automatically sets the current amplitude of said pulses of said second group to be the same as the current amplitude of said pulses of said first group.

6. The intraoperative neural monitoring system recited in claim 4 and further including a repetition selector for said stimulator operable by a user of said intraoperative neural monitoring system, prior to actuation of said activator, to set the number of said pulses in each of said first group and said second group to be 1 to 8 pulses and to alternatively set the number of said pulses in said complete cycle of monophasic electrical stimulation to be 1 to 8 pulses.

7. The intraoperative neural monitoring system recited in claim 6 wherein said repetition selector automatically sets the number of said pulses in said second group to be the same as the number of said pulses in said first group.

8. The intraoperative neural monitoring system recited in claim 4 and further including a pulse width selector for said stimulator operable by a user of said intraoperative neural monitoring system to set said pulses to have a duration in the range of 100 to 500 microseconds.

9. The intraoperative neural monitoring system recited in claim 4 wherein said stimulator delivers said complete cycle of biphasic electrical stimulation with there being a predetermined fixed interval between said first group of pulses and said second group of pulses of about 2 seconds.

10. The intraoperative neural monitoring system recited in claim 4 and further including a delay selector for said stimulator operable by a user of said intraoperative neural monitoring system to set said complete cycle of biphasic electrical stimulation to have a delay between successive pulses in each of said first group and said second group of pulses in the range of 2 to 4 milliseconds and to alternatively set said complete cycle of monophasic electrical stimulation to have a delay between successive pulses in the range of 2 to 4 milliseconds.

11. The intraoperative neural monitoring system recited in claim 1 wherein said power source comprises a power console electrically connectible to said stimulator.

12. An intraoperative neural monitoring system comprising
a power source;
a stimulator powered by said power source to deliver electrical stimulation for application to anatomical tissue, said stimulator being capable of delivering said electrical stimulation as a complete cycle of biphasic electrical stimulation having a first group of one or more positive or negative pulses followed by a second group of one or more pulses of opposite polarity to said pulses of said first group; and an activator for said stimulator actuatable by a user of said intraoperative neural monitoring system completing performance of a multi-step manual actuation procedure with said activator to start delivery of said first group of pulses, said stimulator delivering said complete cycle of biphasic electrical stimulation in its entirety in response to actuation of said activator to start delivery of said first group of pulses;
wherein said stimulator is alternatively capable of delivering said electrical stimulation as a complete cycle of monophasic electrical stimulation having one or more positive or negative pulses, and further including a mode selector for said stimulator operable by a user of said intraoperative neural monitoring system, prior to actuation of said activator, to select said complete cycle of biphasic electrical stimulation for delivery by said stimulator and to alternatively select said complete cycle of monophasic electrical stimulation for delivery by said stimulator, said activator being alternatively actuatable by a user of said intraoperative neural monitoring system completing performance of said multi-step manual actuation procedure with said activator to alternatively start delivery of said complete cycle of monophasic electrical stimulation, said stimulator delivering said complete cycle of monophasic electrical stimulation in its entirety in response to actuation of said activator to start delivery of said complete cycle of monophasic electrical stimulation.

13. The intraoperative neural monitoring system recited in claim 12 wherein said activator is actuatable by a user of said intraoperative neural monitoring system completing performance of a two-step manual actuation procedure with said activator to start delivery of said first group of pulses.

14. The intraoperative neural monitoring system recited in claim 13 wherein said activator comprises a hand switch having a button, and said activator is actuatable by a user of said intraoperative neural monitoring system pressing said button consecutively two times to start delivery of said first group of pulses.

15. The intraoperative neural monitoring system recited in claim 13 wherein said power source comprises a power console electrically connectible to said stimulator, said power console having a touch screen, said activator comprises an activate option and an accept option on said touch screen, and said activator is actuatable by a user of said intraoperative neural monitoring system pressing said activate option and thereafter pressing said accept option to start delivery of said first group of pulses.

16. An intraoperative neural monitoring system comprising
a power console providing a power source and a display screen;
a patient interface unit electrically connectible to said power console, said patient interface unit being connectible to monitoring electrodes placed at areas of a patient's body to detect responses to a first form of electrical stimulation and a second form of electrical stimulation for display on said display screen, said patient interface unit being connectible to monopolar and bipolar stimulating probes for applying said first form of electrical stimulation to anatomical tissue of the patient, said patient interface unit delivering said first form of electrical stimulation up to a current amplitude of about 30 mA;
a stimulator electrically connectible to said power console, said stimulator being connectible to a pair of stimulating electrodes placed at areas of a patient's body for applying said second form of electrical stimulation to anatomical tissue of the patient, said stimulator delivering said second form of electrical stimulation to a first one of the stimulating electrodes for return via a second one of the stimulating electrodes in a positive phase for said second form of electrical stimulation and delivering said second form of electrical stimulation to the second one of the stimulating electrodes for return via the first one of the stimulating electrodes in a negative phase for said second form of electrical stimulation, said stimulator delivering said second form of electrical stimulation up to a current amplitude of about 200 mA;

an activator for said stimulator actuatable by a user of said intraoperative neural monitoring system to start delivery of said second form of electrical stimulation from said stimulator; and a mode selector for said stimulator having a plurality of mode settings alternatively selectable by a user of said intraoperative neural monitoring system to set said stimulator, prior to actuation of said activator, to deliver a finite cycle of said second form of electrical stimulation in a mode corresponding to the selected mode setting, said mode selector having a positive monophasic mode setting to set said stimulator to delivery a finite cycle of said second form of electrical stimulation in a positive monophasic mode having a selected number of pulses all of said positive phase, a negative monophasic mode setting to set said stimulator to deliver a finite cycle of said second form of electrical stimulation in a negative monophasic mode having a selected number of pulses all of said negative phase, a positive leading biphasic mode setting to set said stimulator to deliver a finite cycle of said second form of electrical stimulation in a positive leading biphasic mode having a first group of a selected number of pulses all of said positive phase automatically followed by a second group of a selected number of pulses all of said negative phase, and a negative leading biphasic mode setting to set said stimulator to deliver a finite cycle of said second form of electrical stimulation in a negative leading biphasic mode having a first group of a selected number of pulses all of said negative phase automatically followed by a second group of a selected number of pulses all of said positive phase.

17. The intraoperative neural monitoring system recited in claim 16 wherein said first form of electrical stimulation comprises continuous constant current monophasic DC pulses and said pulses of said second form of electrical stimulation are constant current DC pulses.

18. The intraoperative neural monitoring system recited in claim 17 wherein said intraoperative neural monitoring system further includes means for detecting the duration of said pulses of said second form of electrical stimulation and means for terminating delivery of said second form of electrical stimulation automatically when the duration of a pulse of said second form of electrical stimulation is detected to exceed a predetermined duration.

19. The intraoperative neural monitoring system recited in claim 17 wherein said pulses of said first form of electrical stimulation are selectable to have a pulse width in the range of 50 to 250 microseconds and a rate of 1 to 10 pulses/second, said pulses of said second form of electrical stimulation are selectable to have a pulse width in the range of 100 to 500 microseconds, said number of pulses in said finite cycle of said second form of electrical stimulation for said positive monophasic mode and said negative monophasic mode is selectable to be in the range of 1 to 8 pulses, said number of pulses in said finite cycle of said second form of electrical stimulation for said positive leading biphasic mode and said negative leading biphasic mode is selectable to be in the range of 1 to 8 pulses for said first group and an equal number of pulses for said second group, said finite cycle of said second form of electrical stimulation for said biphasic modes includes a fixed interval of about 2 seconds between said first group and said second group of pulses, said finite cycle of said second form of electrical stimulation for said biphasic modes includes a delay between successive pulses in said first group and said second group, said finite cycle of said second form of electrical stimulation for said monophasic modes includes said delay between successive pulses, and said delay is selectable to be in the range of 2 to 4 milliseconds.

20. The intraoperative neural monitoring system recited in claim 19 wherein said display screen comprises a touch screen presenting a plurality of displays including control options for selecting said pulse width for said first and second forms of electrical stimulation, said current amplitude for said first and second forms of electrical stimulation, said rate for said first form of electrical stimulation, said number of pulses for said first and second groups of pulses for said second form of electrical stimulation, said delay for said first and second forms of electrical stimulation, and for operating said mode selector.

21. The intraoperative neural monitoring system recited in claim 16 wherein actuation of said activator to start delivery of said second form of electrical stimulation effects delivery of said finite cycle of said second form of electrical stimulation in its entirety.

22. The intraoperative neural monitoring system recited in claim 16 wherein said patient interface unit includes a plurality of monitoring channels each connectible to a pair of monitoring electrodes.

23. The intraoperative neural monitoring system recited in claim 22 wherein said display screen includes a first monitoring display for displaying waveforms representing responses detected by the monitoring electrodes for each of said monitoring channels when said first form of electrical stimulation is applied to the patient and a second monitoring display for displaying waveforms representing responses detected by the monitoring electrodes for each of said monitoring channels when said second form of electrical stimulation is applied to the patient.

24. The intraoperative neural monitoring system recited in claim 23 wherein said second monitoring display includes a waveform display area for simultaneously displaying responses detected by the monitoring electrodes in response to said first group of pulses and said second group of pulses for said biphasic modes.

25. The intraoperative neural monitoring system recited in claim 23 wherein said second monitoring display includes a waveform display area for simultaneously displaying responses detected by monitoring electrodes on the left and right sides of the patient's body.

26. The intraoperative neural monitoring system recited in claim 23 wherein said display screen comprises a touch screen, and said touch screen includes a control option for selecting an event threshold by which detected responses above said event threshold are signaled.

27. The intraoperative neural monitoring system recited in claim 23 wherein said display screen comprises a touch screen, and said touch screen includes a control option for setting an artifact delay by which the influence of artifact on detected responses is distinguished.

* * * * *